United States Patent
Dahl et al.

(10) Patent No.: US 10,731,214 B2
(45) Date of Patent: *Aug. 4, 2020

(54) NUCLEIC ACID PROBE AND METHOD OF DETECTING GENOMIC FRAGMENTS

(71) Applicant: Vanadis Diagnostics, Sollentuna (SE)

(72) Inventors: Carl Oscar Fredrik Dahl, Sigtuna (SE); Olof John Ericsson, Uppsala (SE)

(73) Assignee: VANADIS DIAGNOSTICS, Sollentuna (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/250,892

(22) Filed: Jan. 17, 2019

(65) Prior Publication Data

US 2019/0194748 A1 Jun. 27, 2019

Related U.S. Application Data

(63) Continuation of application No. 15/035,466, filed as application No. PCT/IB2014/003061 on Nov. 26, 2014, now Pat. No. 10,240,198.

(30) Foreign Application Priority Data

Dec. 2, 2013 (GB) .................................. 1321191.7

(51) Int. Cl.
*C12Q 1/6876* (2018.01)
*C12Q 1/6816* (2018.01)

(52) U.S. Cl.
CPC ......... *C12Q 1/6876* (2013.01); *C12Q 1/6816* (2013.01)

(58) Field of Classification Search
None
See application file for complete search history.

(56) References Cited

U.S. PATENT DOCUMENTS

| 5,854,033 A | 12/1998 | Lizardi et al. |
|---|---|---|
| 2003/0022167 A1 | 1/2003 | Alsmadi et al. |
| 2003/0032024 A1 | 2/2003 | Lizardi |
| 2004/0166514 A1 | 8/2004 | Puskas |
| 2007/0087355 A1 | 4/2007 | Barrett |
| 2009/0004666 A1 | 1/2009 | Tanabe et al. |
| 2009/0004701 A1 | 1/2009 | Faham et al. |
| 2013/0224729 A1 | 8/2013 | Church et al. |

FOREIGN PATENT DOCUMENTS

| CN | 102899417 | 1/2013 |
|---|---|---|
| EP | 2653559 | 10/2013 |
| GB | 2492042 | 12/2012 |
| JP | 2007537751 | 12/2007 |
| JP | 2008518639 | 6/2008 |
| JP | 2008527979 | 7/2008 |
| JP | 2009535050 | 10/2009 |
| JP | 2016537989 | 12/2016 |
| RU | 2478716 | 4/2013 |
| WO | 01/94625 | 12/2001 |
| WO | 2001094625 | 3/2003 |
| WO | 2003044216 | 5/2003 |
| WO | WO 2004/057017 | 7/2004 |
| WO | 2005047547 | 5/2005 |
| WO | 2005111236 | 11/2005 |
| WO | 20070087355 | 4/2007 |
| WO | WO 2007/083766 | 7/2007 |
| WO | 2009029742 | 3/2009 |
| WO | 2011009941 | 1/2011 |
| WO | 2011142836 | 11/2011 |
| WO | 2012019200 | 11/2012 |
| WO | WO 2012/168803 | 12/2012 |
| WO | 2013079649 | 6/2013 |
| WO | 2014165267 | 12/2014 |
| WO | 2015083001 | 6/2015 |

(Continued)

OTHER PUBLICATIONS

Goransson (Nucleic Acids Research (2009) vol. 37, e7 and supplemental content).*
Dahl et al., "Multiplex amplification enabled by selective circularization of large sets of genomic DNA fragments" Nucleic Acids Res, Apr. 2005, p. e71, vol. 33, No. 8.
Fredriksson et al., "Multiplex amplification of all coding sequences within 10 cancer genes by Gene-Collector" Nucleic Acids Res, Apr. 2007, p. e47, vol. 35, No. 7.
Guo et al., "Simultaneous Detection of Trisomies 13, 18, and 21 with Multiplex Litigation-Dependent Probe Amplification-Based Real-Time PCR" Clinical Chemistry, Sep. 2010, pp. 1451-1459, vol. 56, No. 9.

(Continued)

*Primary Examiner* — Steven Pohnert
(74) *Attorney, Agent, or Firm* — James S. Keddie; Bozicevic, Field & Francis LLP

(57) ABSTRACT

Provided herein, among other things, is a method of processing a nucleic acid sample. In some embodiments, the method comprises a) hybridizing a sample comprising a target fragment to a nucleic acid probe comprising: i. a head sequence and a tail sequence, wherein the head and tail sequences are at the ends of a first oligonucleotide molecule; and ii. a splint sequence comprising, in order: an upstream flanking sequence that is complementary to the head sequence; a target complementary sequence that is complementary to the target fragment; and a downstream flanking sequence that is complementary to the tail sequence; thereby producing a hybridization product in which the ends of the target fragment are ligatably adjacent to the ends of the head and tail sequences in the first oligonucleotide molecule; and b) ligating the ends of the target fragment to the ends of the head and tail sequences of the first oligonucleotide molecule, thereby producing a cyclic product that comprises the target fragment and the head and tail sequences. Probes and kits for performing the method are also provided.

15 Claims, 7 Drawing Sheets

Specification includes a Sequence Listing.

(56) References Cited

FOREIGN PATENT DOCUMENTS

WO          2015083002          6/2015

OTHER PUBLICATIONS

Hardenbol et al., "Multiplexed genotyping with sequence-tagged molecular inversion probes" Nat Biotechnol, Jun. 2003, pp. 673-678, vol. 21, No. 6.
Hardenbol et al., "Highly multiplexed molecular inversion probe genotyping: over 10,000 targeted SNP's genotyped in a single tube assay" Genome Res, Feb. 2005, pp. 269-275, vol. 15, No. 2.
Marciniak et al., "Coupled rolling circle amplification loop-mediated amplification for rapid detection of short DNA sequences" BioTechniques, Sep. 2008, pp. 275-280, vol. 45, No. 3.
Shen et al., "Multiplex target capture with double-stranded DNA probes" Genome Med, 2013, p. 50, vol. 5, No. 5.
Amann, et al., "Combination of 16S rRNA-Targeted Oligonucleotide Probes with Flow Cytometry for Analyzing Mixed Microbial Populations", Applied and Environmental Microbiology, 1990, 56(6): 1919-1925.
Eriksson, et al., "Multiplex and quantifiable detection of nucleic acid from pathogenic fungi using padlock probes, generic real time PCR and specific suspension array readout", Journal of Microbiological Methods, 2009, 78: 195-202.
Nilsson, et al., "Real-time monitoring of rolling-circle amplification using a modified molecular beacon design", Nucleic Acids Research, 2002, 30(14): e66.
Zhou, et al., "Two-color, rolling-circle amplification on antibody microarrays for sensitive, multiplexed serum-protein measurements", Genome Biology, 2004, 5:R28.
Lizardi et al., "Mutation detection and single-molecule counting using isothermal rolling-circle amplification", Nature Genetics, 1998, 19(3):225-232.
Database Embl [Online], "Human centromeric alphoid repeat DNA unit (h3)", 1986, retrieved from EBI accession No. EM_STD:X02953 Database accession No. X02953.
Absalan et al., "Molecular Inversion Probe Assay", Methods in Molecular Biology, 2007, vol. 396: Comparative Genomics, vol. 2, pp. 315-330.
Pont-Kingdon et al., "Rapid Detection of Aneuploidy (Trisomy 21) by Allele Quantification Combined with Melting Curves Analysis of Single-Nucleotide Polymorphism Loci", Molecular Diagnostics and Genetics, Clinical Chemistry, 2003, 49(7): 1087-1094.
"TOPO Cloning Technology", Thermo Fisher Scientific, 2015.
Dahlgren et al., "Analysis of siRNA specificity on targets with double-nucleotide mismatches", Nucleic Acids Research, 2008, 36(9):e53, pp. 1-7.
Sethupathy et al., "Human microRNA-155 on Chromosome 21 Differentially Interacts with Its Polymorphic Target in the AGTR2 3' Untranslated Region: A Mechanism for Functional Single-Nucleotide Polymorphisms Related to Phenotypes", The American Journal of Human Genetics, 2007, 81: 405-413.
Lagos-Quintana et al., "Identification of Novel Genes Coding for Small Expressed RNAs", Science, 2001, 294: 853-858.
Akhras et al., "Connector Inversion Probe Technology: A Powerful One-Primer Multiplex DNA Amplification System or Numerous Scientific Applications", PLoS ONE, 2007, 2(9): e915. doi:10.1371/journal.pone.0000915.

* cited by examiner

NUCLEIC ACID PROBE AND METHOD OF DETECTING GENOMIC FRAGMENTS

CROSS-REFERENCING

This application is divisional of U.S. patent application Ser. No. 15/035,466, filed on May 9, 2016, which is a § 371 filing of PCT/IB2014/003061, filed on Nov. 26, 2014, which claims the benefit of UK Application No: 1321191.7, filed on Dec. 2, 2013, which applications are incorporated by reference herein.

FIELD OF THE INVENTION

The present disclosure relates to probes for detecting specific nucleic acid sequences in biological samples, especially probes for use in multiplex methods of detecting multiple specific sequences in parallel, and to methods in which such probes are used for detecting fragments of nucleic acid. In particular, the present disclosure relates to targeting DNA fragments from specific chromosomes for downstream analysis.

BACKGROUND

The human haploid genome contains 3 billion base pairs packaged in 23 chromosomes, and the diploid genome has 6 billion base pairs in 23 pairs of chromosomes. The rapidity and convenience of modern sequencing technology enables many diagnostic questions to be approached using high-throughput sequencing of an individual's entire genome or of the full quantity of DNA in a sample. However, for many DNA diagnostics applications, it is only necessary to investigate a subset of the genome, focussing on the region or regions known to be associated with the particular disorders under investigation.

A number of techniques have been described for reducing the complexity of the genome before analysis. Where only a single, short region of the genome is required to be analysed, this may be done using straightforward PCR to amplify the sequence using primers to known regions on either side. However, when it is desired to amplify many regions of a genomic sample for analysis, amplification artefacts can arise as a result of performing multiple different amplifications together in the same reaction mixture.

WO2003/044216 (Parallele Bioscience, Inc.) and US20090004701A1 (Malek Faham) described a method of multiplex amplification of target nucleic acids, in which common oligonucleotide primers were ligated to sites internal to single-stranded nucleic acid fragments. The common priming sites were appended to each of a plurality of different target sequences to allow their stoichiometric amplification.

WO2005/111236 (Olink AB) also described a method of identifying sequences in the human genome by amplifying specific target sequences. The method involved fragmenting the genomic sample into fragments having at least one defined end sequence. Selector constructs, all comprising a primer pair motif, were brought in contact with the fragments. After ligation, the selected target sequences were amplified in parallel using a primer-pair specific for the primer-pair motif common to the selectors. The selector constructs described in WO2005/111236 had a long oligonucleotide hybridised to a short oligonucleotide, each selector construct having one or two protruding ends complementary to a defined end sequence of a fragment containing the target sequence. Contacting the selectors with the target fragments resulted in hybridisation of the target fragment between protruding ends of the selector or selectors. In the case of a single selector with two protruding ends this hybridisation produced a circularised construct. In the case of a pair of selectors each with one protruding end this formed a linear construct. Ligation and sequencing of the selector constructs containing the target fragments allowed the target sequence to be determined. Since the selector constructs hybridise only to the end portions of the fragment containing the target sequence (or to one end portion and one internal portion), the method allowed selection of target sequences that differed in the non-hybridising portions, so that each selector molecule could hybridise to a variety of different target sequences. The identity of the exact target was then determined by amplifying and sequencing the constructs. WO2005/111236 proposed using the selectors in methods of analysing genetic variability or for DNA copy number measurements.

GB2492042 described a variation of the selector method, in which the fragments were contacted with a partially double-stranded probe comprising a selector oligonucleotide and at least one vector oligonucleotide. The selector oligonucleotide contained two non-adjacent regions specific for the target fragment and a non-target specific region which comprised at least two binding sites for the vector oligonucleotide. The vector oligonucleotide was not complementary to the target sequence, and included a nucleotide sequence complementary to the vector-binding site on the selector oligonucleotide. The vector oligonucleotide also contained elements for detection/enrichment. In the method, complementary portions of the probe oligonucleotides were hybridised to the target fragment, followed by ligating the vector oligonucleotide(s) and target to produce a probe-target fragment hybrid, which was then detected.

A development of the selector technology was described in WO2011/009941 (Olink Genomics AB), describing ligation of one end of a fragment of digested genomic DNA to a probe. Compared with the earlier selector probes, which involved binding to two regions of the target fragment and where the sequence to be isolated was typically bounded by two regions of known sequence, the probes in WO2011/009941 were described for use where there was only one known region of sequence. Some embodiments of the probes in WO2011/009941 contained elements for immobilisation to a solid phase. Ligation of the target nucleic acid fragment to the probe resulted in a stable capture of the target fragment and allowed the use of highly stringent washing steps to remove non-ligated fragments, resulting in a high specificity.

Also known are padlock probes. Padlock probes are linear oligonucleotides with target complementary sequences at the ends and a non-target complementary sequence in between. When hybridised to the correct target DNA sequence, the two ends of the probe are brought together head to tail and can be joined by DNA ligase. Ligation is inhibited by mismatches at the ligation junction, so successful ligation of the padlock probe depends on highly specific hybridisation to the target sequence, allowing the probe to distinguish between highly similar target sequences and selectively padlock its exact target. As a consequence of the helical nature of double stranded DNA, the circularised probe molecule is catenated to the target DNA strand.

It was known to amplify the circularised padlock probes using rolling circle replication, also known as rolling circle amplification. Rolling circle replication was described in U.S. Pat. No. 5,854,033 (Lizardi). Rolling circle replication is an amplification of a circular nucleic acid molecule using a strand displacing DNA polymerase, resulting in large DNA molecules containing tandem repeats of the amplified sequence. The DNA polymerase catalyses primer extension and strand displacement in a processive rolling circle polymerisation reaction that proceeds as long as desired. It results in an amplification of the circularised probe sequence orders of magnitude higher than a single cycle of PCR replication and other amplification techniques in which each cycle is limited to a doubling of the number of copies of a target sequence. Additional amplification can be obtained using a cascade of strand displacement reactions.

Fredriksson et al. (*Nucleic Acids Res.* 35(7):e47 2007) described "Gene-Collector", a method for multiplex amplification of nucleic acids using collector probes which contain adjacent sequences complementary to the cognate primer end sequences of desired PCR products, so that binding of the collector probes to the PCR products brings the ends of the PCR products together to form a DNA circle. Universal amplification is then performed using rolling circle amplification to generate a final product of concatamers of target sequences. This method allows the correct amplicons in a multiplex PCR reaction to be selectively detected, because the end sequences of the correct amplicons are a cognate primer pair and are circularised by the collector probe, whereas PCR artefacts combining a primer from one pair with a primer from another pair are not circularised.

SUMMARY OF THE INVENTION

The present disclosure provides improved methods and probes for analysing nucleic acid fragments, such as fragmented genomic DNA. Some embodiments of the invention relate to probes and to their use in methods of testing samples for the presence of a target single stranded nucleic acid fragments. Some embodiments of the invention relate to probes which comprise a targeting oligonucleotide containing a target-complementary sequence which is the complement of the target fragment and a flanking sequence adjacent to the target-complementary sequence, and an oligonucleotide sequence having a free 5' or 3' end, wherein hybridisation between the fragment and the probe templates the target fragment for ligation to the free 5' or 3' end of the oligonucleotide sequence.

Some embodiments of the invention further relate to probes which hybridise along the length of a single stranded nucleic acid fragment and ligate to each end of the fragment. Such probes comprise an oligonucleotide sequence having a free 5' end and an oligonucleotide sequence having a free 3' end, for ligation to each end of the target fragment. The ligation product is then detected, allowing a highly specific targeting and detection of the defined nucleic acid fragments.

A method according to some embodiments of the invention may comprise digesting DNA to fragments with defined sequence, denaturing the resulting DNA fragments to single stranded fragments (targets) and mixing the targets with probes as described herein. Hybridisation of the targets to the probes produces templates for ligation to specifically connect the target to a corresponding probe to generate either a circle or a linear ligation product. The ligation products may then be enriched, for example by exonucleases or solid-phase chemistry, and optionally amplified by rolling circle amplification, PCR, or other DNA amplification methods.

A key advantage of some embodiments of the present invention lies in the analysis of a multitude of DNA fragments in parallel. A multitude of DNA fragments may be specifically targeted and selected for downstream analysis. This is particularly useful for the non-invasive prenatal testing (NIPT) of cell-free foetal DNA in the maternal bloodstream, where counting of thousands of chromosome-specific DNA fragments produces a very precise quantification.

In one aspect, a method of testing a sample for the presence of a target nucleic acid is provided. The method typically involves generating defined target nucleic acid fragments, contacting the sample with a probe that hybridises along the length of the target fragment and provides ligatable junctions in both the 3' and 5' end of the fragment, ligating the target fragment to the probe at both the 3' and 5' end, and then detecting the new nucleic acid molecule formed by the double ligation event.

One aspect provides a method of testing a sample for the presence of a target nucleic acid, comprising:

(i) providing a sample of fragmented nucleic acid (ii) providing denaturing conditions under which the target fragment is single stranded (iii) contacting the sample with a nucleic acid probe comprising a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and the target fragment, if present, hybridises to the target-complementary sequence, thereby positioning the ends of the target fragment in juxtaposition with the 5' end of the head sequence and the 3' end of the tail sequence (v) providing conditions for ligation so that, if the target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, and (vi) detecting whether the product of double ligation is present, wherein detecting the product of double ligation indicates the presence of the target fragment in the sample.

In contrast with most other DNA selection and detection approaches, the present method may be particularly useful when the entire nucleic acid fragment is pre-defined or pre-determined—that is, when the sequence of the target fragment is known in advance. In some implementations of the present method, the target fragment is the product of a specific fragmentation of nucleic acid, rather than a random fragmentation such as may be produced by physical means such as shearing or sonication. Specific fragmentation of nucleic acid may be achieved using restriction enzymes, PCR, or other sequence directed fragment end definition.

It is desirable for the targeting oligonucleotide to contact the entire target fragment, to ensure specific binding of the precise target sequence. This contrasts with earlier approaches where probes were designed to hybridise with an end or ends of the fragment and/or to an internal region but not to bind along the length of the target fragment. Indeed, limited binding to the target fragment was a deliberate design feature in many earlier probes, since it allowed fragments to be targeted and detected when their sequence was only partly known. By specifically targeting fragments of known sequence—subject to the possibility of slight sequence variability resulting from different alleles in a population, where applicable—the probes and methods of the present method may allow precise binding and detection of the desired target fragment with very low risk of false-positive results.

The double ligation of the target fragment further may contribute to the high specificity of the method. The probe becomes ligated to the target sequence at each end, i.e., to the 5' and 3' ends of the single stranded fragment of nucleic acid. Thus, the ends of the target which were specifically generated by fragmentation may be specifically detected by sequence-specific ligation to the head and tail sequences. The sequence-specific nature of the ligation is achieved through the requirement for hybridisation of both the target fragment and the head and tail sequences to the targeting oligonucleotide, and through the sensitivity of DNA ligase which is inhibited by base pair mismatches. Hybridisation of the target fragment to the targeting oligonucleotide contributes to the specificity of the binding but, in contrast with the ligation reactions which provides highest selectivity with respect to mismatches at the 3' and 5' ends of the target fragment, the hybridisation is destabilised the most by internal mismatches in the central part of the target.

The targeting oligonucleotide acts to template ligation of the target fragment to the head and tail sequences. The head and tail sequences hybridise to the flanking sequences, defining a gap between the 5' end of the head sequence and the 3' end of the tail sequence. The target fragment hybridises to the target-complementary sequence in the gap, thereby positioning the ends of the target fragment in juxtaposition with the 5' end of the head sequence and the 3' end of the tail sequences. Preferably, the annealing of the target fragment and the head and tail sequences to the probe generates two perfectly matched ligatable junctions. The product of double ligation is then a continuous strand of nucleic acid comprising the head and tail sequences and the target fragment.

A number of possible designs of the probe are contemplated. For example, the 5' and 3' ends for ligation to the target fragment may be provided by head and tail sequences on two separate backbone oligonucleotides, or by head and tail sequences at respective ends of a single backbone oligonucleotide which loops to position the target fragment between the 5' and 3' ends.

In the first case (two separate backbone oligonucleotides), ligation of the target fragment to the two backbone oligonucleotides produces a linear strand of nucleic acid comprising the target fragment between the head and tail sequences.

In the second case (single looped backbone oligonucleotide), ligation of the target fragment produces a circle of nucleic acid comprising the target sequence between the head and tail sequences.

In further versions, one or both of the head and tail sequences may be provided on the targeting oligonucleotide itself, so that the targeting oligonucleotide forms a looped structure under annealing conditions. Depending on the design, the product of double ligation in such cases may either be a linear or a circular nucleic acid molecule.

Detection of the product is dependent on successful ligation of the target fragment to the head and tail sequences to form a continuous strand of nucleic acid. In general, the product of double ligation is detected using an approach that requires both ligation events to occur in order to generate a signal. For example, detection may comprise amplification across both ligation junctions (e.g., by PCR or, for circularising embodiments of the probe, rolling circle replication), or capturing the continuous nucleic acid strand at one end and detecting its other end. The covalent attachment of the target fragment to the probe by ligation forms a strong bond, so stringent washing may be used to remove non-ligated nucleic acids in which the head and tail sequences are not covalently attached, their mutual hybridisation to the targeting oligonucleotide being disrupted by the washing.

These features of the method and the probe enable a highly specific selection of target fragments. When the methods are applied for multiplex detection of a plurality of target fragments in parallel, a very precise detection and quantification of the target nucleic acid is possible. As a result of its high specificity, the present method may be especially suitable for diagnostic use in small samples and/or for detecting very small differences in relative amounts of different target nucleic acids, for example in diagnosing aneuploidies in foetal chromosomes from a sample of maternal blood or in detecting the presence of trace amounts of tumour DNA in a sample of normal tissue from a patient or detection of nucleic acid fragments from infectious agents.

Having a highly specific target fragment recognition enables use of a relatively high probe concentration without generating false positive signals, thereby increasing the yield and efficiency of the reaction. This may be of high importance in diagnostic applications where low variability is important and targets may be present in low numbers for example in NIPT by analysis of cell free DNA, detection of cell free circulating cancer DNA and detection of DNA from infectious agents. Some embodiments of the present method enables highly specific analysis of short DNA fragments, which is of importance in applications for analysis of fragmented DNA like cell free DNA in blood, or formalin fixed paraffin embedded DNA.

With reference to FIGS. 3 and 4, provided herein, among other things, is a method of processing a nucleic acid sample. In some embodiments, the method may comprise: a) hybridizing a sample (e.g., a sample that has been digested with a restriction enzyme) comprising a target fragment (a "DNA target") to a nucleic acid probe comprising: i. a head sequence and a tail sequence, wherein the head and tail sequences are at the ends of a first oligonucleotide molecule; and ii. a splint sequence (where the term "splint sequence" is intended to refer to a sequence in an oligonucleotide that, when hybridized to two or more other polynucleotides, acts as a "splint" to position the polynucleotides next to one another so that they can be ligated together, as illustrated in FIGS. 3 and 4). As shown in FIGS. 3 and 4, the splint sequence (which is referred to as a "targeting oligonucleotide" in some cases) used in this method contains an upstream flanking sequence that is complementary to the head sequence; a target complementary sequence that is complementary to the target fragment; and a downstream flanking sequence that is complementary to the tail sequence. This hybridization step produces a hybridization product in which the ends of the target fragment are ligatably adjacent to the ends of the head and tail sequences in the first oligonucleotide molecule, where the term "ligatably adjacent" in the context of two sequences that are ligatably adjacent to one another, means that there are no intervening nucleotides between two oligonucleotides and they can be ligated to one another using a ligase. The next step of the method comprises b) ligating the ends of the target fragment to the ends of the head and tail sequences of the first oligonucleotide molecule, thereby producing a cyclic product that comprises the target fragment and the head and tail sequences. This ligation step is illustrated in FIG. 1 (although, as illustrated in FIGS. 3 and 4, the method may be implemented a variety of different ways and, as such, the nucleic acid probe used in the first step of the method can be composed of one or two oligonucleotides).

Circularized products provide a significant advantage for detection because they can be amplified by rolling circle amplification (RCA). RCA produces hundreds or thousands of copies of a circularized product in a single molecule, thereby effectively amplifying the circularized product and making it relatively easy to detect using, e.g., labeled oligonucleotides that hybridize to a motif in the product.

As illustrated in FIG. 1, the method may further comprise amplifying the cyclic product by rolling circle amplification using a primer that hybridizes to a sequence in the nucleic acid probe (e.g., a head sequence, a tail sequence, or a sequence therebetween). In these embodiments, the method may further comprise quantifying the number of rolling circle amplification products produced, thereby providing an estimate of the amount of said target fragment in the sample. In these embodiments, the products may be amplified by rolling circle amplification using primer that is complementary to a sequence somewhere in the cyclic product) to produce a plurality of RCA products, e.g., product corresponding to a single, "cloned" fragment. The number of rolling circle amplification products can be estimated by, e.g., distributing the RCA products on the surface of a support (a slide), hybridizing the RCA products using labelled oligonucleotides (e.g., fluorescently labelled oligonucleotides) and then counting the number of discrete signals in an area of the support by microscopy, e.g., fluorescence microscopy. The labelling can be done before or after the products have been distributed on the support and, because each RCA product contains thousands of copies of the same sequences, there should be thousands of binding sites for the labelled oligonucleotides, thereby increasing the signal. In multiplex embodiments (e.g., in which RCA products corresponding to two different chromosomes are being counted), the RCA products corresponding to one chromosome can be labelled with one fluorophore and the RCA products corresponding to another chromosome can be labelled with a different fluorophore, thereby allowing the different RCA products to be separately counted.

Quantifying signals from individual RCA products is significant because, in many applications (e.g., non-invasive pre-natal diagnosis by analysis of cell free DNA), the number of fragments corresponding to particular chromosomes (e.g., chromosome 21) needs to be determined quire accurately and without bias. Typical analysis methods use PCR which, as is well known, is a very biased procedure in that some sequences are amplified much higher efficiencies than others. This makes PCR-based strategies impractical for many diagnostic efforts.

In alternative embodiments and as illustrated in FIG. 1, the target fragment may be amplified by PCR and quantified. As would be apparent, the flanking sequences that are added to the target fragment and/or the PCR primers may be compatible with use in, e.g., Illumina's reversible terminator method, Roche's pyrosequencing method (454), Life Technologies' sequencing by ligation (the SOLiD platform) or Life Technologies' Ion Torrent platform. Examples of such methods are described in the following references: Margulies et al (Nature 2005 437: 376-80); Ronaghi et al (Analytical Biochemistry 1996 242: 84-9); Shendure (Science 2005 309: 1728); Imelfort et al (Brief Bioinform. 2009 10:609-18); Fox et al (Methods Mol Biol. 2009; 553:79-108); Appleby et al (Methods Mol Biol. 2009; 513:19-39) and Morozova (Genomics. 2008 92:255-64), which are incorporated by reference for the general descriptions of the methods and the particular steps of the methods, including all starting products, reagents, and final products for each of the steps. In these embodiments, the cyclic products may be amplified and sequenced, and the abundance of the fragments in the sample can be estimated by counting the number of sequence reads corresponding to the fragments.

In certain embodiments and as illustrated in FIG. 3, the splint sequence may in a different molecule to the head and tail sequences, i.e., a "second" oligonucleotide molecule. As such, the the nucleic acid probe used at the beginning of the method may be composed of two oligonucleotides (a "backbone" and a "targeting" oligonucleotide, as illustrated in FIG. 3).

In other embodiments and as illustrated in FIG. 4, the splint sequence may be in the same molecule as the head and tail sequences, i.e., in the "first" oligonucleotide molecule. As such, the nucleic acid probe used at the beginning of the method may be composed of a single oligonucleotide.

The target-complementary sequence may be of any length, depending on the length of the target complementary sequence in the nucleic acid probe. In some embodiments, the target-complementary sequence is 10 to 100, e.g., 10 to 50 or 10 to 30 nucleotides in length. As noted below, the target-complementary sequence contains one or more mismatches (e.g., 1, 2, 3, 4, 5 or 6 or more, up to 10 or more) to the target fragment and, in certain cases, the reverse complement of the target-complementary sequence may be at least 80%, at least 90% or at least 95% identical to the target fragment.

The flanking sequences may be of any length, depending on design. In some embodiments, the flanking sequences are 10 and 40 nucleotides, e.g., 10 and 30 nucleotides, in length.

In some embodiments, the sample may contain fragments of genomic DNA, e.g., genomic DNA from virtually any organism, including, but not limited to, plants, animals (e.g., reptiles, mammals, insects, worms, fish, etc.), tissue samples, bacteria, fungi (e.g., yeast), phage, viruses, cadaveric tissue, archaeological/ancient samples, etc. In certain embodiments, the genomic DNA used in the method may be derived from a mammal, where in certain embodiments the mammal is a human. In exemplary embodiments, the genomic sample may contain genomic DNA from a mammalian cell, such as, a human, mouse, rat, or monkey cell. The sample may be made from cultured cells or cells of a clinical sample, e.g., a tissue biopsy, scrape or lavage or cells of a forensic sample (i.e., cells of a sample collected at a crime scene). In particular embodiments, the nucleic acid sample may be obtained from a biological sample such as cells, tissues, bodily fluids, and stool. Bodily fluids of interest include but are not limited to, blood, serum, plasma, saliva, mucous, phlegm, cerebral spinal fluid, pleural fluid, tears, lactal duct fluid, lymph, sputum, cerebrospinal fluid, synovial fluid, urine, amniotic fluid, and semen. In particular embodiments, a sample may be obtained from a subject, e.g., a human. In some embodiments, the sample analyzed may be a sample of cell-free DNA obtained from blood, e.g., from the blood of a pregnant female. In certain embodiments, the genomic DNA may be amplified, e.g., using a whole genome amplification method, prior to fragmentation.

In embodiments, in which the splint sequence is in a second oligonucleotide molecule (as shown in FIG. 3), the second oligonucleotide may additionally comprise a capture moiety that can be employed to enrich for the cyclic product. In these embodiments, the method may comprise: c) immobilizing the cyclic product by binding the capture moiety to a solid phase; and d) washing the solid phase to remove unligated nucleic acid and other reaction components; thereby enriching for the cyclic product. For example, the second oligonucleotide may contain a biotin moiety, e.g., biotin or a biotin analogue such as desthiobiotin, oxybiotin, 2'-iminobiotin, diaminobiotin, biotin sulfoxide, biocytin, etc., with or without a linker, e.g., -LC-biotin, -LC-LC-Biotin, -SLC-Biotin or -PEGn-Biotin where n is 3-12, and the cyclic products can be enriched using a substrate that is coupled to streptavidin. Biotin binds to streptavidin with an affinity of at least $10^{-8}$M.

For non-invasive pre-natal testing embodiments, the target fragment may be from human chromosome 21, 13 or 18.

In some embodiments, the method comprises hybridizing the sample with a set of at least 50 (e.g., at least 100, at least 200, at least 500, at least 1,000, at least 2,000 or at least 5,000) of said probes, wherein said probes target different fragments on the same chromosome (e.g., human chromosome 21, 13 or 18), and wherein the method results in a plurality of cyclic products that comprises the target fragments. The number of cyclic products produced can be quantified by, e.g., amplifying them using RCA and counting the number of RCA products, as described above.

In some embodiments, the method comprises hybridizing the sample with a first set and a second set of said sets of nucleic acid probes, wherein the first and second sets of probes target (i.e., hybridize to fragments of and ligate to produce cyclic products, as described above) a first chromosome in the sample and a second chromosome in the sample, respectively, amplifying the cyclic products by rolling circle amplification (RCA) and comparing the number of RCA products corresponding to the first chromosome to the number of RCA products corresponding to the first chromosome, thereby providing an estimate of the relative amounts of DNA from the chromosomes in the sample.

In some embodiments, the method comprises hybridizing the sample with a first set and a second set of said sets of nucleic acid probes, wherein the first and second sets of probes target (i.e., hybridize to fragments of and ligate to produce cyclic products, as described above) a first region and a second region of a chromosome in the sample, respectively, amplifying the cyclic products by rolling circle amplification (RCA) and comparing the number of RCA products corresponding to the first chromosomal region to the number of RCA products corresponding to the second chromosomal region, thereby providing an estimate of the relative amounts of DNA from the chromosomal regions in the sample. This embodiment may be used to identify, e.g., deletions or duplications, for example.

Also provided herein is composition comprising a nucleic acid probe comprising: i. a head sequence and a tail sequence, wherein the head and tail sequences are at opposite ends of a first oligonucleotide molecule; and ii. a splint sequence comprising, in order: an upstream flanking sequence that is complementary to the head sequence, a target complementary sequence that is complementary to a target fragment in the human genome; and a downstream flanking sequence that is complementary to the tail sequence; wherein the probe is designed so that, when the first oligonucleotide, the splint sequence, and the target fragment are hybridized to one another, the ends of the target fragment are ligatably adjacent to the ends of the head and tail sequences in the first oligonucleotide molecule. In certain embodiments, the composition may comprise a first set of at least 50 (e.g., at least 100, at least 200, at least 500, at least 1,000, at least 2,000 or at least 5,000) of the nucleic acid probes, wherein the target complementary sequences of the probes are complementary to different target fragments of a first human chromosome (e.g., chromosome is 21, 13 or 18).

In certain embodiments, the composition may comprise a second set of at least 50 (e.g., at least 100, at least 200, at least 500, at least 1,000, at least 2,000 or at least 5,000) of said nucleic acid probes, wherein the target complementary sequences of the probes in the second set of probes are complementary to different target fragments of a second human chromosome. In some embodiments, the first human chromosome may be chromosome 21 and the second human chromosome may be chromosome 13 or 18. In some cases, the second human chromosome is not chromosome 21, 13 or 18.

BRIEF DESCRIPTION OF THE DRAWINGS

The skilled artisan will understand that the drawings, described below, are for illustration purposes only. The drawings are not intended to limit the scope of the present teachings in any way.

DETAILED DESCRIPTION

The Target Nucleic Acid Fragment

Figure 1:
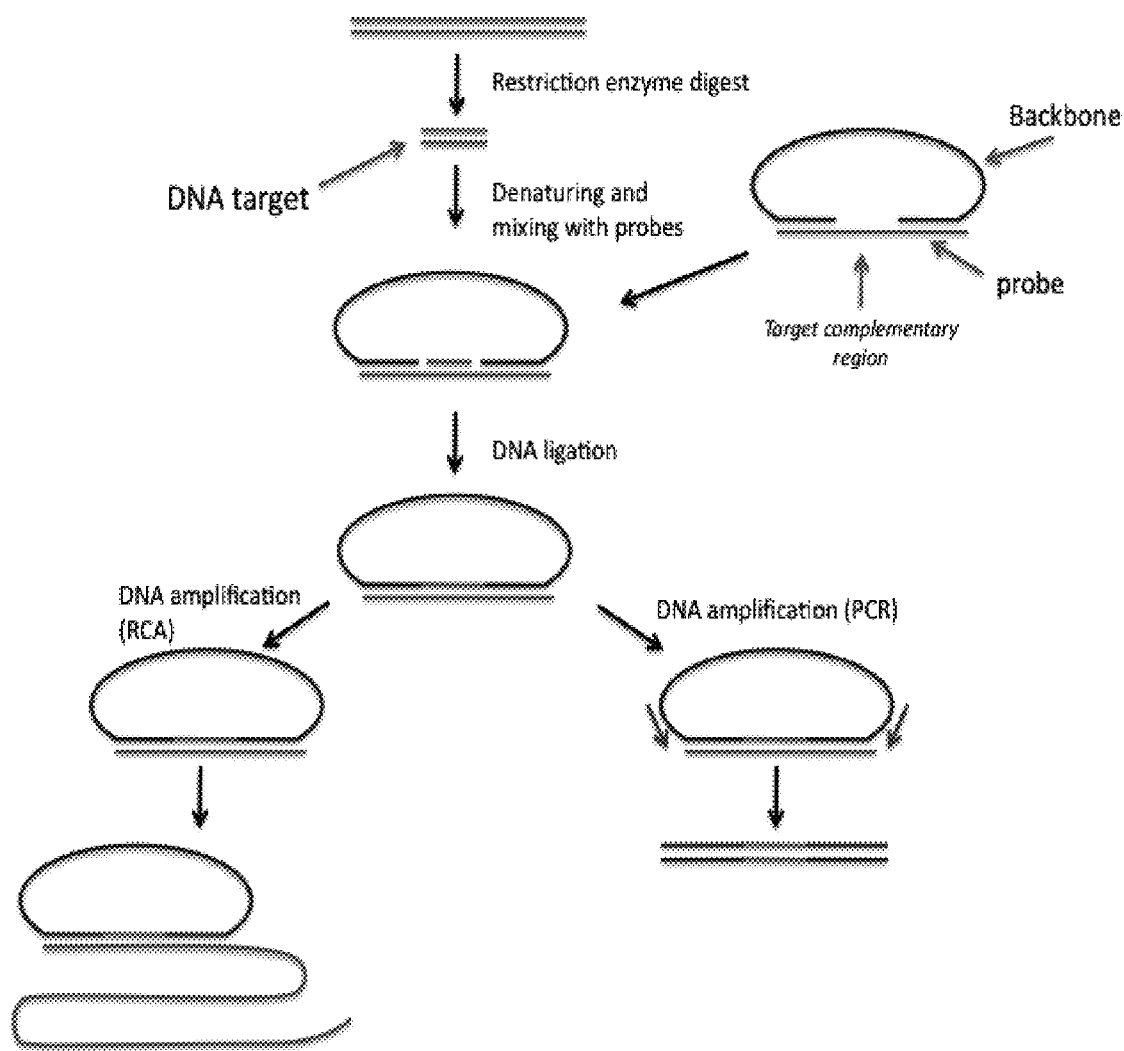
FIG. 1 schematically illustrates one embodiment of the subject method in which a circular DNA molecule is formed and amplified by RCA or PCR.

The target fragment which is bound by the probe is a single stranded fragment of nucleic acid. In some embodiments, the present methods bind target fragments whose sequence is pre-defined. The sequence of the entire fragment including the ends may be known. Known fragments of pre-defined sequence can be produced by specific, rather than random, fragmentation of nucleic acid. Specific fragmentation methods include digestion with restriction enzymes, PCR (e.g., multiplex PCR), and other methods of sequence directed fragment end definition, including other enzymes, ribozymes, or a combination of such techniques.

One method of fragmentation is digestion with a restriction endonuclease or a combination of two or more restriction endonucleases. Thus, the sample of fragmented nucleic acid may be a restriction enzyme digest and the target fragment may be a restriction fragment.

A variety of specific nucleic acid cleaving enzymes are known and any suitable enzyme may be used in the present invention, including enzymes which cleave at a pre-defined position within a specific nucleic acid sequence, or endonucleolytic enzymes which cleave either after or before a specific nucleic acid recognition sequence and nicking enzymes. Catalytic nucleic acids, such as ribozymes, can be used as well for DNA fragmentation. The enzymes may cleave double stranded nucleic acid to produce a blunt end or a sticky end, or may cleave a single strand of nucleic acid. Various types of restriction enzymes are known, including Type I, Type II, Type III, Type IV and Type V. Suitable enzymes or combinations of enzymes can be selected for use in the method as desired. For example, nucleic acid in a sample (e.g. 10 ng of DNA) may be digested with restriction enzyme (e.g. 1 U) in corresponding compatible restriction enzyme buffer. The reaction may be incubated under suitable conditions (e.g. 37° C. for 1 hour), followed by enzymatic deactivation (e.g. at 80° C. for 20 minutes).

Another convenient method of providing the fragmented nucleic acid is to use primers for amplification of specific linear sequences from the nucleic acid. Multiplex PCR can be used, treating the nucleic acid with multiple specific primer pairs to amplify multiple specific fragments. In this case, the ends of the target fragment correspond to the sequences of the pair of primers.

For many diagnostic and other applications, the sample is a sample of fragmented chromosomes (e.g., human chromosomes or microbial chromosomes). The target fragment may be a genome fragment specific to one chromosome of an organism's genome. In other words, the target fragment may be found only in one chromosome of the genome and not in other chromosomes of that genome. Commonly, the method will be used for analysis of the human genome, in which case the target fragment may be a fragment specific to one human chromosome, i.e., found in that chromosome and not in other human chromosomes. For example, the fragment may be specific to chromosome 21.

The target fragment may be specific to one locus of a chromosome. Accordingly, it may be found in that chromosomal locus and not in other loci of the same chromosome or other chromosomes of the same genome. For example, the fragment may be specific to one locus of a human chromosome.

A given species of nucleic acid in a sample may encompass some variability, for example a sample may comprise chromosomes of different individuals, such as nucleic acid obtained from maternal blood which contains maternal DNA and foetal DNA. Here the species of interest may be a particular chromosome, but it is convenient to detect all copies of that chromosome whether of foetal or maternal origin. Thus, a species of interest may be one chromosome or chromosomal locus, and the target sequences are found in that chromosome or locus in both maternal and foetal copies of the chromosome or chromosomal locus.

Samples of nucleic acid may be provided in any suitable way, for example as samples of biological tissue or fluid from patients. Samples may be blood samples, whole blood, plasma, or serum, tissue samples, e.g., formalin fixed paraffin embedded samples of tissue, or may be samples of nucleic acid extracted from blood or tissue.

The sample may be any sample that contains nucleic acid. The nucleic acid contained in the sample may be DNA and/or RNA. The sample may be complex, e.g. whole genomic DNA, or cDNA from a whole organism, tissue or cell population, or a fraction thereof. In this regard it may, for example, be a direct product of a nucleic acid isolation procedure, or of a cell lysis procedure, or it may be further be fractionated or purified in some way, e.g. it may contain nucleic acids which have been partially or fully separated in some way, or treated in any way, e.g. RNA to produce cDNA. The sample may be from any eukaryotic or prokaryotic or viral source, e.g. may be microbial (for example bacterial or fungal), plant, or animal. Preferably the sample is of human origin, e.g., human genomic DNA. The sample may be a tissue or blood sample from an animal, where the nucleic acid to be detected is microbial, e.g., bacterial, viral or fungal. For methods relating to non-invasive prenatal diagnostics, the sample is derived from the blood of a pregnant woman and comprises foetal DNA. In other examples, the nucleic acid to be detected or quantified is tumour associated DNA.

Usually, the method may be performed on the samples in vitro. Accordingly, the methods generally do not include diagnosis carried out in vivo on the human or animal body or methods of treatment of the human or animal body by surgery or therapy. Nevertheless, the results of the in vitro diagnostic methods may be used to inform the subsequent treatment of patients.

Denaturing the Target Nucleic Acid

The probe recognises and binds the target nucleic acid in single stranded form, through hybridisation between the single stranded fragment and the target-complementary sequence of the targeting oligonucleotide. Therefore, if the target fragment in the sample is not already single stranded, denaturing conditions should be provided to separate the single stranded target fragment from its complementary nucleic acid strand.

The denaturing conditions may be a sufficiently high temperature to separate the target fragment from its complementary sequence. Denaturing conditions may be incubation at 95° C. for a suitable time, e.g. 10 minutes. Alternatively chemical denaturation may be performed.

Complementarity

A method of testing a sample for the presence of a target fragment may comprise contacting the sample with a nucleic acid probe, wherein the probe comprises a targeting oligonucleotide containing a target-complementary sequence, which is the complement of the target fragment, and a flanking sequence adjacent to the target-complementary sequence and an oligonucleotide sequence having a free 5' or 3' end, wherein the oligonucleotide sequence is complementary to the flanking sequence.

Suitable concentrations of probes may be determined based on the concentration (or expected concentration) of the target fragment or target fragments in the sample. As illustrated in the Examples, probes may be added to the sample at a concentration of 10 pM per probe. Where a sample is contacted with multiple probes (e.g. a set of probes), concentrations of the individual probes may be 10 pM. Preferably, probes are used in excess of the expected concentration of the nucleic acid species of interest to be detected or quantified. Use of excess probe should ensure that all copies of target sequences present in the sample are recognised. This maximises the sensitivity of detection. Also, where methods involve quantification, it ensures that the detection of the ligation products or cumulative signal from a set of probes is proportional to the quantity of target sequences in the sample.

Under annealing conditions, the target fragment (if present) hybridises to the target complementary sequence of the targeting strand and the oligonucleotide sequence hybridises to the flanking sequence, so that the free 5' or 3' end of the oligonucleotide sequence is in juxtaposition with the 3' or 5' end of the target fragment respectively. Thus, the targeting oligonucleotide templates the target fragment for ligation to the oligonucleotide sequence. The 3' end of the target fragment may be ligated to a 5' end of a head sequence and the 5' end of the target fragment may be ligated to a 3' end of a tail sequence in a double ligation event.

In probes according to the present invention, maximum specificity for the target fragment is achieved if the target-complementary sequence is the exact complement of the target fragment, so that there is perfect hybridisation between them. However, this is not essential in all cases, and a small degree of mismatching may be accepted, for example to allow detection of fragments which exhibit allelic variation where it is desired to detect the fragment regardless of the exact allele present in the sample. Alternatively, multiple probes can be designed for variant sequences. This can enable both detection and discrimination of different alleles or mutations. Probes according to the present invention are most advantageously used in multiplex methods where large numbers of different probes are included in a reaction. Within such a plurality of probes, it is envisaged that the majority of probes will have perfect complementarity for their target fragments but some probes may bind targets with minor mismatches.

Preferably, the target-complementary sequence has fewer than 5 base pair mismatches with the target fragment. There may optionally be one, two, three or four base pair mismatches between the target fragment and the target-complementary sequence. A mismatch may be a point at which a corresponding base is absent from one sequence, so that the complementary sequence forms a loop at the mismatched point, or may occur where a non-complementary nucleotide is present in one sequence and so does not pair with the base at the corresponding position of the other sequence. Where there is an incorrect base pairing, i.e., a pairing of A or T with C or G, hydrogen bonding does not take place between the bases of the two strands, although hybridisation will still take place between the target fragment and the target complementary sequence of the targeting oligonucleotide due to base-pairing between the nucleotides neighbouring the mismatch. Mismatches may be wobble bases. A wobble base would normally correspond to a position in the target complementary sequence that pairs with a position of known genetic variation in the target fragment. The probe may be synthesised by adding one or several dideoxynucleotides during the specific synthesis cycle for the wobble base position. This is typically the case for traditional oligonucleotide synthesis. Alternatively multiple separate probes may be produced, one for each genetic variant. This is typically the case if probes are synthesised using microarray based synthesis. A wobble base may correspond to single nucleotide differences between codons, where the different codons encode the same amino acid.

In general, longer target-complementary sequences for hybridising longer target fragments may tolerate a higher number of mismatches compared with shorter target-complementary sequences. The target-complementary sequence may, for example, have at most 1 in 8, 1 in 9 or 1 in 10 base pair mismatches with the target fragment. Any such mismatches should be restricted to the internal region of the target complementary sequence and target fragment, so that they do not inhibit ligation or sequence specific target fragmentation by e.g. restriction enzyme digestion. Accordingly, preferably there is perfect complementarity between the target fragment and the target complementary sequence in the terminal 6 to 8 nucleotides, preferably the terminal 10 nucleotides at each end of the target fragment.

Generally, the target fragment and the target-complementary sequence are of the same length. The full length of the target fragment is thus bound by the target complementary sequence. Hybridisation of the target fragment to the targeting oligonucleotide represents a single binding event between the two nucleic acid molecules, contrasting with probes which bind the two ends of a target molecule or to two non-adjacent regions of the target.

The target-complementary sequence may have a length of at least 10 nucleotides, for example at least 15 nucleotides. It may be up to 20, 25, 30, 35 or 40 nucleotides long. Preferred ranges include 10-20 nucleotides, 10-30 nucleotides, and 10-40 nucleotides. Such relatively short target-complementary sequences are suitable for binding correspondingly short fragments. The short sequence contributes to the specificity of the double ligation reaction, since DNA ligase is sensitive to base pair mismatches and will preferentially ligate perfectly matched sequences. Where mismatches are present in the footprint of DNA ligase bound to the double stranded sequence, the sequences may not be ligated, which provides an additional proofreading step ensuring high specificity in detecting the target fragment in preference to fragments of different but similar sequence. DNA ligase typically has a footprint of 6 to 8 bases on each side of the nick. Therefore, if the fragment is 20 bases, 12 to 16 of the bases will be covered by ligase specificity.

The probe hybridisation will discriminate against mismatches especially in the central part of the hybridised sequence while the ligation will discriminate against mismatches at the ends of the target fragment. Together this generates a highly specific fragment detection.

The targeting oligonucleotide is longer than the target fragment since it includes the flanking sequences as well as the target-complementary sequence, and it may further include one or more custom sequences. A custom sequence is not complementary to other regions of the probe or to the target fragment—in other words it does not hybridise to other regions of the probe (outside the custom sequence) or to the target fragment under annealing conditions. The upstream flanking region is upstream of or 5' of the target-complementary sequence in the targeting oligonucleotide. The downstream flanking region is downstream of or 3' of the target-complementary sequence in the targeting oligonucleotide. Accordingly, the target-complementary sequence is internal to the targeting oligonucleotide and does not include an end of the targeting oligonucleotide, since it is flanked by the upstream and downstream flanking sequences.

The double stranded sequence produced by hybridisation of the target fragment and the target-complementary sequence may be considered a hybrid double stranded sequence, since it is a hybrid of the target and the probe. Typically the double stranded sequence adopts a double helical conformation, in which the target fragment is one strand and the targeting oligonucleotide is the other strand of the double helix. The hybrid double stranded sequence is flanked by the upstream and downstream flanking sequences of the targeting oligonucleotide, which in turn hybridise to the head and tail sequences to produce double stranded sequences. Again, these typically adopt the normal double helical conformation of double stranded nucleic acid.

The upstream and downstream flanking sequences are preferably different from each other, i.e., preferably have different sequences. It is preferred that the head sequence is complementary to the upstream flanking sequence but not to the downstream flanking sequence, and that the tail sequence is complementary to the downstream flanking sequence but not to the upstream flanking sequence. This ensures that the head and tail sequences hybridise only to the upstream and downstream flanking sequences respectively.

The head sequence will usually be the same length as the upstream flanking sequence. The tail sequence will usually be the same length as the downstream flanking sequence.

Normal lengths for the flanking sequences are between 10 and 40 nucleotides, for example 10-20 or 10-30 nucleotides. The flanking sequences may be the same length as each other. One or both flanking sequences may be the same length as the target-complementary sequence. The upstream and/or downstream flanking sequence may thus have a length of at least 10 nucleotides, for example at least 15 nucleotides. It may be up to 20, 25, 30, 35 or 40 nucleotides long.

Preferably, the head sequence is the complement of the upstream sequence. Preferably, the tail sequence is the complement of the downstream sequence. Perfect matching of the sequences is desirable for optimum binding of the probe so that the head and tail sequences are correctly positioned for ligation to the target fragment. Optionally, however, there may be one, two three or four base pair mismatches between the head sequence and the upstream flanking sequence, and/or between the tail sequence and the downstream flanking sequence. Preferably, there are fewer than 5 base pair mismatches.

Other than the target-complementary sequence, the probe should usually not be complementary to the target fragment or to other nucleic acids that may be present in the sample. This is to avoid unwanted hybridisation of the probe to nucleic acid other than the target. Thus, if the probe is for binding a fragment of human genomic DNA, the probe may be designed so that sequences other than the target-complementary sequence are not complementary to human genomic DNA, so that the probe only hybridises to the target fragment and not to other nucleic acid in the sample.

Annealing and Ligation

The target fragment is ligated in a highly specific reaction at both ends. Since the target fragment is typically the product of a specific fragmentation of nucleic acid, these ends will usually have a specific, pre-determined sequence. In the ligation step, these ends are specifically detected by sequence-dependent ligation to the head and tail sequences respectively. Preferably, binding of the target fragment to the probe creates two perfectly matched ligatable junctions, one between the 3' end of the target fragment and the 5' end of the head sequence and one between the 5' end of the target fragment and the 3' end of the tail sequence.

Ligation of a 5' end of nucleic acid to a 3' end of nucleic acid can occur when the two ends are base paired to adjacent nucleotides of a complementary sequence. Base pairing of the respective end nucleotides to the adjacent nucleotides forms a nucleic acid strand containing a nick between the two ends. Ligation of the two ends can be catalysed by DNA ligase. Providing conditions for ligation will therefore usually comprise providing a DNA ligase enzyme and reaction conditions under which the DNA ligase ligates the two ends to form a continuous nucleic acid strand, closing the nick. A number of ligase enzymes are commercially available, such as Ampligase (Epicentre), for which suitable conditions are to add 1 U enzyme and incubate at 55° C. for 1 hour in ligase buffer.

The targeting oligonucleotide templates the target fragment for ligation to the head and tail sequences, due to the location of the target-complementary sequence between the flanking sequences. Under annealing conditions in the presence of the target fragment, the head and tail sequences hybridise to the flanking sequences, defining a gap between the 5' end of the head sequence and the 3' end of the tail sequence. The target fragment hybridises to the target-complementary sequence in the gap. Thus, hybridisation of the head and tail sequences and the target fragment to the targeting oligonucleotide positions the 3' end of the target fragment in juxtaposition with the 5' end of the head sequence, and positions the 5' end of the target fragment in juxtaposition with the 3' end of the tail sequence.

Positioning of two ends in juxtaposition provides a substrate for DNA ligase to ligate the ends together. It is preferable that the 5' end of the head sequence and the 3' end of the target fragment hybridise to adjacent nucleotides of the targeting oligonucleotide, and the 3' end of the tail sequence and the 5' end of the target fragment hybridise to adjacent nucleotides of the targeting oligonucleotide. Accordingly, the upstream flanking sequence may be immediately adjacent to the target-complementary sequence, with no intervening nucleotides. Similarly, the downstream flanking sequence may be immediately adjacent to the target-complementary sequence, with no intervening nucleotides. Adjacent 3' and 5' ends can be directly ligated by DNA ligase sealing the nick between them to form a continuous nucleic acid strand.

The product of the double ligation, i.e., the product of ligating both the head sequence and the tail sequence to the target fragment, is a continuous strand of nucleic acid. It is continuous in the sense that it contains no nicks or gaps, so all nucleotides in the strand are covalently joined.

The probe may be designed so that the continuous strand of nucleic acid comprising the head and tail sequences and the target fragment is a circle of nucleic acid. The term circle here refers to the topology of the strand being a closed loop, with no free end.

Under annealing conditions in the presence of the target fragment, the head and tail sequences hybridise to the flanking sequences, defining a gap between the 5' end of the head sequence and the 3' end of the tail sequence. The target fragment hybridises to the target-complementary sequence in the gap, thereby positioning the ends of the target fragment in juxtaposition with the 5' end of the head sequence and the 3' end of the tail sequences, and completing a circle of nucleic acid which comprises the target fragment and the head and tail sequences.

The nucleic acid molecules which form the circle have their ends in juxtaposition. Ligation of the ends produces the continuous circular strand of nucleic acid comprising at least the head and tail sequences and the target fragment.

Figure 3:
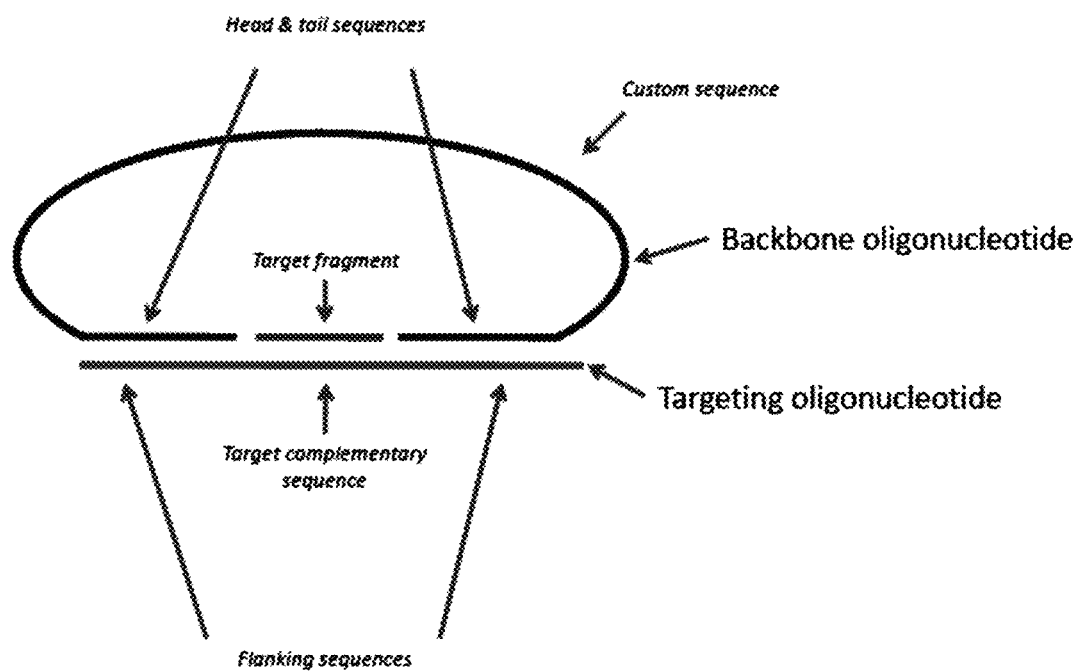
FIG. 3 shows a probe comprising a circularised backbone oligonucleotide bound to its target fragment. The probe is illustrated in two versions, A and B.
Figure 3:
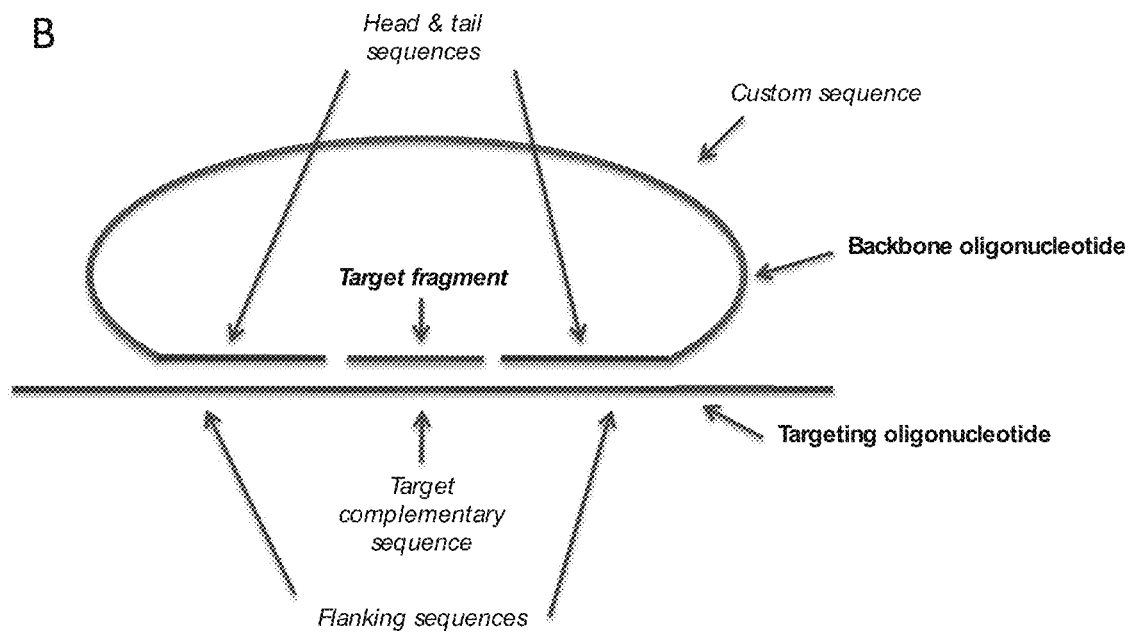

Probes which form a circle of nucleic acid include probes in which the head and tail sequences are provided on a single nucleic acid molecule. For example, in addition to the targeting oligonucleotide the probe may comprise a backbone oligonucleotide having the head and tail sequences at its 5' end 3' ends respectively, wherein the head and tail sequences of the backbone oligonucleotide bind in trans to the flanking sequences of the targeting oligonucleotide under the annealing conditions. The backbone oligonucleotide may comprise a custom sequence between the head and tail sequences. FIG. 3 illustrates embodiments of such probes. Alternatively, the head and tail sequences of the backbone oligonucleotide may be adjacent, with no custom sequence between them.

Figure 4:
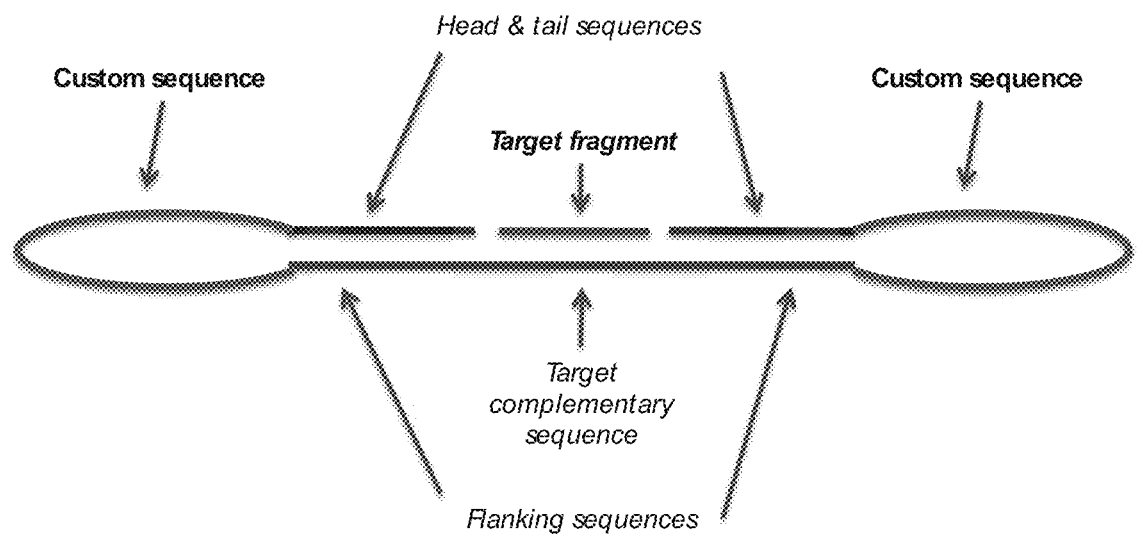
FIG. 4 shows a circularised single oligonucleotide probe with bound target fragment.

In another example, the head and tail sequences may be at ends of the targeting oligonucleotide and bind in cis to the flanking sequences under the annealing conditions. The targeting oligonucleotide may comprise a custom sequence between the targeting oligonucleotide and the head and/or tail sequence. FIG. 4 illustrates an embodiment of such a probe.

Figure 5:
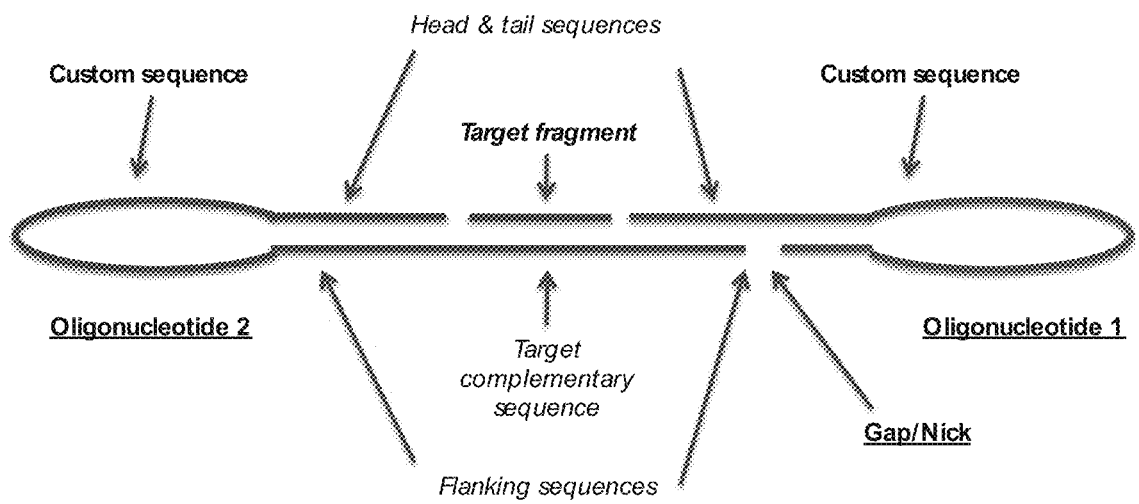
FIG. 5 shows a circularised double looped probe composed of a targeting oligonucleotide and a looped backbone oligonucleotide, with bound target fragment.

Probes which form a circle of nucleic acid also include probes in which the head and tail sequences are provided on different nucleic acid molecules. In such cases, the circle of nucleic acid which forms under the annealing conditions will comprise at least three nucleic acid molecules—the target fragment, the head sequence and the tail sequence. The ends of the nucleic acid molecules will all be in juxtaposition, as previously noted. More than two ligation reactions are required to form the continuous circular strand of nucleic acid in such cases. An example is where the tail sequence is the 3' end of the targeting oligonucleotide, and the probe comprises a backbone oligonucleotide having the head sequence at its 5' end. Under the annealing conditions the tail sequence binds in cis to the downstream flanking sequence of the targeting oligonucleotide, and the head sequence of the backbone oligonucleotide binds in trans to the upstream flanking sequence of the targeting oligonucleotide. Binding in cis means that the binding takes place on the same nucleic acid molecule, i.e., a single strand of nucleic acid forms a three dimensional structure in which different regions are brought together and hybridise. Binding in trans means that the binding takes place between different nucleic acid molecules. Optionally, the backbone oligonucleotide comprises a pair of inverted repeat sequences which form a hairpin structure under annealing conditions, thereby positioning the 3' end of the backbone oligonucleotide in juxtaposition with the 5' end of the targeting oligonucleotide. There is a nick between the two ends. A probe of this type is illustrated in FIG. 5. When conditions for ligation are provided, the 5' end of the targeting oligonucleotide is ligated to the 3' end of the backbone oligonucleotide. The product of double ligation is a circle of nucleic acid comprising the targeting oligonucleotide, the target fragment and the backbone oligonucleotide. Alternatively, where there is a gap between the 5' end of the targeting oligonucleotide and the 3' end of the backbone oligonucleotide, the probe shown in FIG. 5 will not be circularised by ligation—instead the continuous strand of nucleic acid comprising the head and tail sequences and the target fragment is a linear strand of nucleic acid.

The probe may alternatively be arranged in the opposite orientation so that the head sequence is at the 5' end of the targeting oligonucleotide and the probe comprises a backbone oligonucleotide having the tail sequence at its 3' end. In this case, under the annealing conditions the head sequence binds in cis to the upstream flanking sequence of the targeting oligonucleotide, and the tail sequence of the backbone oligonucleotide binds in trans to the downstream flanking sequence of the targeting oligonucleotide. Again, the backbone oligonucleotide may comprise a pair of inverted repeat sequences which form a hairpin structure under annealing conditions to position the 5' end of the backbone oligonucleotide in juxtaposition with the 3' end of the targeting oligonucleotide. The 3' end of the targeting oligonucleotide is then ligated to the 5' end of the backbone oligonucleotide so that the product of double ligation is a circle of nucleic acid comprising the targeting oligonucleotide, the target fragment and the backbone oligonucleotide. Alternatively, as noted above, the annealing may position the 5' end of the backbone oligonucleotide near the 3' end of the targeting oligonucleotide but separated by a gap of one or more nucleotides. The ligated product will then be a continuous linear strand of nucleic acid comprising the head and tail sequences and the target fragment.

The backbone oligonucleotide may comprise a custom sequence between the inverted repeat sequence, so that under the annealing conditions the backbone oligonucleotide forms a hairpin loop, as illustrated in FIG. 5.

As noted, probes may be designed so that the continuous strand of nucleic acid comprising the head and tail sequences and the target fragment is a linear strand of nucleic acid. Under annealing conditions in the presence of the target fragment, the head and tail sequences hybridise to the flanking sequences, defining a gap between the 5' end of the head sequence and the 3' end of the tail sequence. The target fragment hybridises to the target-complementary sequence in the gap, thereby positioning the ends of the target fragment in juxtaposition with the 5' end of the head sequence and the 3' end of the tail sequences, and completing a strand of nucleic acid which comprises the target fragment and the head and tail sequences. The nucleic acid molecules which form the strand have their ends in juxtaposition. The term juxtaposition has been discussed elsewhere. There is a nick between the ends to be ligated. Ligation of the ends produces the continuous strand of nucleic acid comprising at least the head and tail sequences and the target fragment.

Figure 6:
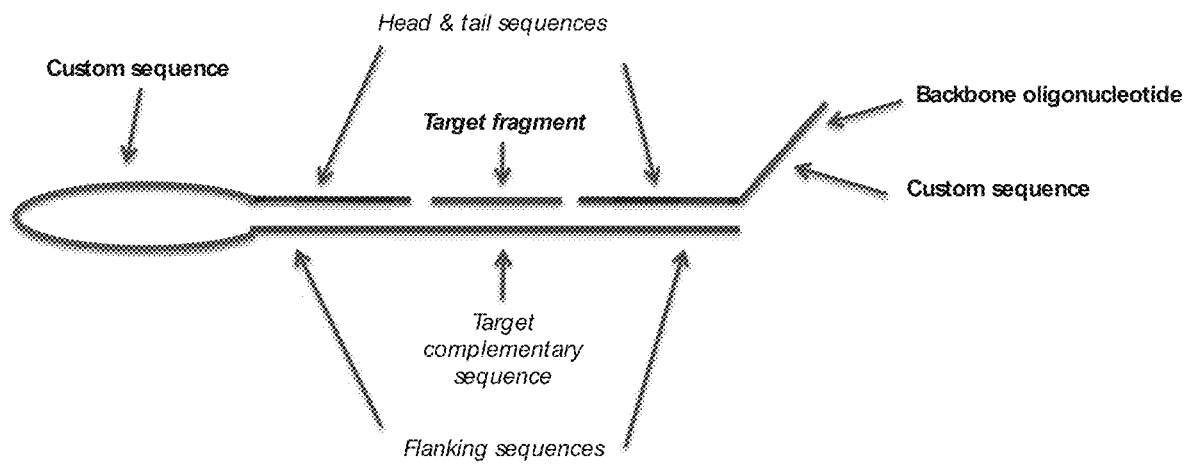
FIG. 6 shows a linear looped probe composed of a targeting oligonucleotide and a linear backbone oligonucleotide, with bound target fragment.

The probe may comprise a targeting oligonucleotide having the tail sequence at its 3' end and a linear backbone oligonucleotide having the head sequence at its 5' end. Under annealing conditions, the tail sequence binds in cis to the downstream flanking sequence of the targeting oligonucleotide, and the head sequence of the backbone oligonucleotide binds in trans to the upstream flanking sequence of the targeting oligonucleotide. The targeting oligonucleotide may comprise a custom sequence between the downstream flanking sequence and the tail sequence, so that under the annealing conditions the targeting oligonucleotide forms a hairpin loop. The linear strand of nucleic acid formed under annealing conditions comprises the backbone oligonucleotide, the target fragment and the targeting oligonucleotide. FIG. 6 illustrates this arrangement.

The probe may equally be arranged in the reverse orientation, where the head sequence is at the 5' end of the targeting oligonucleotide, and the probe comprises a backbone oligonucleotide having the tail sequence at its 3' end. In this case the head sequence binds in cis to the upstream flanking sequence of the targeting oligonucleotide and the tail sequence of the backbone oligonucleotide binds in trans to the downstream flanking sequence of the targeting oligonucleotide.

Figure 7:
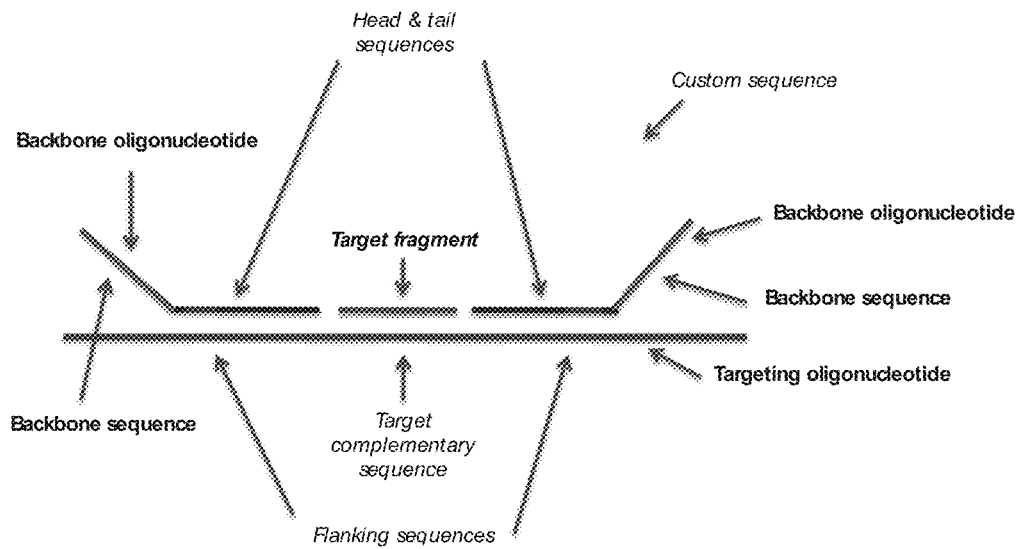
FIG. 7 shows a linear probe comprising two backbone oligonucleotides, with bound target fragment.

Another form of probe which forms a linear nucleic acid strand as the product of ligation is a probe comprising the head and tail sequences on separate backbone oligonucleotides. Such a probe may comprise a backbone oligonucleotide comprising a head sequence having a free 5' end, and a backbone oligonucleotide comprising a tail sequence having a free 3' end, wherein under the annealing conditions the head and tail sequences bind in trans to the flanking sequences of the targeting oligonucleotide. One or both backbone oligonucleotides may further comprise a custom sequence. FIG. 7 illustrates probes of this type.

Preferably, the oligonucleotides of the probe in its unligated form are linear. So, preferably the targeting oligonucleotide is a linear nucleic acid molecule. For probes including one or more backbone oligonucleotides, these are also preferably linear. This allows convenient differentiation between ligated and unligated probes where a circle of DNA is formed only as a result of successful ligation of the circularising embodiments of the probe. Linear nucleic acid molecules are not amplified by rolling circle replication.

Detection

After providing conditions under which the target fragment, if present, is ligated to the probe, a detection step is performed to determine whether or not such ligation has occurred. This indicates whether or not the target fragment was present in the sample. Thus, detection of product is dependent on successful ligation of the target fragment to the head and tail sequences to form the continuous strand of nucleic acid. The detection step therefore generally involves detecting a signal that requires the presence of both ligation junctions. For example, detection may comprise amplification across both ligation junctions (e.g., by PCR or, for circularising embodiments of the probe, rolling circle replication), or capturing the continuous nucleic acid strand at one end and detecting its other end.

Optionally, a method may include enriching the product of double ligation before detection. Products may be enriched by amplification and/or by solid phase chemistry. Circular nucleic acid products may be selectively enriched by treating the sample with exonuclease (e.g., Lambda exonuclease) to digest linear nucleic acid products. In general, exonuclease degradation may be used to enrich for ligation products when the ligation products are protected from exonuclease degradation. Exonuclease should then be deactivated (e.g. by heat) before any subsequent step involving polymerisation, e.g. before rolling circle amplification. As illustrated in Example 1, 1 U Exonuclease may be added to remove non-reacted probes and fragments. Suitable conditions are incubation at 37° C. for 1 hour in corresponding exonuclease buffer, followed by enzyme inactivation at 80° C. for 20 minutes. Where capture/detect methods are used, ligation products may be enriched by capturing the products on a solid phase via the capture moiety. As illustrated in Example 2, a solution containing linear ligation products may be mixed with 10 ml M-280 streptavidin coated magnetic beads (Invitrogen) in Tris-HCl (pH 7.5), 3.5 mM EDTA and 0.07% Tween-20 in a final volume of 200 ml, and incubated at room temperature for 15 minutes. After incubation, the beads are collected using a ring magnet and supernatant is removed. Other ways of enriching for ligation products include specifically size-selecting ligation products.

A convenient way to detect the product of double ligation to provide conditions for amplification and to test for the presence of the amplification product. Several amplification approaches are possible, such as NASPA, LAMP, T7 amplification, PCR or, where the continuous strand is a circle, rolling circle replication. The step of detecting the product of double ligation may comprise providing conditions for amplification across the first and second ligation junctions of the continuous strand of nucleic acid, and detecting whether an amplification product is present. Ligation products may be amplified by clonal amplification. Suitable amplification techniques include rolling circle amplification (see below), bridge PCR (Adessi C, et al., Nucleic Acids Res. 2000 Oct. 15; 28(20):E87), emulsion PCR (digital PCR in emulsions was described by Dressman et al., Proc Natl Acad Sci USA. 2003 Jul. 22; 100(15):8817-22. Epub 2003 Jul. 11) and digital PCR (Vogelstein & Kinzler, Proc Natl Acad Sci USA. 1999 Aug. 3; 96(16):9236-41). Clonal localised amplification in gels was described by Mitra & Church, Nucleic Acids Res. 1999 Dec. 15; 27(24): e34.

Where the product of double ligation is a circle of nucleic acid, a convenient way to detect the product is to provide conditions for rolling circle replication and to detect whether a product of rolling circle replication is present. The product of rolling circle replication is dependent on double ligation to provide the circle of nucleic acid for amplification. Rolling circle replication was described in U.S. Pat. No. 5,854,033 (Lizardi) and Fire & Xu, Proc Natl Acad Sci USA. 1995 May 9; 92(10):4641-5. Rolling circle replication is an amplification of a circular nucleic acid molecule using a strand displacing DNA polymerase, resulting in large DNA molecules containing tandem repeats of the amplified sequence. The DNA polymerase catalyses primer extension and strand displacement in a processive rolling circle polymerisation reaction that proceeds as long as desired. It results in an amplification of the circularised probe sequence orders of magnitude higher than a single cycle of PCR replication and other amplification techniques in which each cycle is limited to a doubling of the number of copies of a target sequence. Additional amplification can be obtained using a cascade of strand displacement reactions. Rolling circle replication may be hyper branched rolling circle replication. Hyperbranched RCA was described by Lizardi et al., Nat Genet. 1998 July; 19(3):225-32. Conditions for rolling circle replication are illustrated in the Examples, for example incubation with 1 U of phi29 polymerase (New England Biolabs) can be added in corresponding phi29 buffer and nucleotides (dNTPs) at 37° C. for 1 hour.

Following rolling circle replication, the amplified probe sequences can be detected and quantified using any of the conventional detection systems for nucleic acids such as detection of fluorescent labels, enzyme-linked detection systems, antibody-mediated label detection, and detection of radioactive labels. Preferably, a rolling circle amplification product is detected by hybridisation of a labelled detection oligonucleotide to a motif in the RCA product, e.g. a motif in a custom sequence of the probe. Because the amplified product is directly proportional to the amount of target sequence present in a sample, quantitative measurements reliably represent the amount of a target sequence in a sample. Major advantages of this method are that the ligation step can be manipulated to obtain allelic discrimination, the DNA replication step is isothermal, and signals are strictly quantitative because the amplification reaction is linear and is catalysed by a highly processive enzyme. In multiplex assays, the primer oligonucleotide used for the DNA polymerase reaction can be the same for all probes.

For probes in which the head and tail sequences are on separate nucleic acid molecules, it may be convenient to use capture/detect methods. The product of double ligation contains the head and tail sequences in a single nucleic acid molecule (the continuous strand), whereas unligated probes do not. Accordingly, the product of double ligation may be specifically detected by capturing the nucleic acid molecule containing the head sequence, washing to remove unligated probe nucleic acid, then detecting the presence of the tail sequence in the captured fraction. Alternatively, the product of double ligation may be detected by capturing the nucleic acid molecule containing the tail sequence, washing to remove unligated probe nucleic acid, then detecting the presence of the head sequence in the captured fraction.

Detection is specific to the ligated probes, since the head and tail sequences in the unligated probes are connected only by hybridisation between the nucleic acids and are separated by washing, whereas the ligated probes contain the head and tail sequences in a continuous nucleic acid strand, i.e., covalently joined.

A probe may be modified to carry a capture moiety. The capture moiety may permit attachment to a solid substrate such as a bead. A suitable capture moiety is biotin, which pairs with streptavidin, allowing the modified probe nucleic acid to be isolated on the solid substrate coated with streptavidin. Where a probe comprises a backbone oligonucleotide containing either the head or tail sequence, and a separate nucleic acid (targeting oligonucleotide, or a second backbone oligonucleotide) containing the tail or head respectively, either of these nucleic acid molecules may carry a capture moiety, for example may be biotinylated. It may be convenient to provide the probe with the capture moiety before combining the probe with the sample. Alternatively, the capture moiety may be introduced after the ligation step.

Where one nucleic acid molecule in the probe carries a capture moiety, the other may carry a label. It is possible to use the nucleic acid sequence itself as a label, for example to specifically detect the presence of the head sequence (where the tail is captured) or the tail sequence (where the head is captured) or to detect a custom sequence which is unique to the nucleic acid molecule to be detected. A complementary oligonucleotide may be used for detection. Alternatively the nucleic acid may carry a heterogeneous label such as a fluorophore. The heterogeneous label is not part of the nucleic acid itself. Other labels that can be used include quantum dots, bioluminescence, signal generating enzyme cascades like tyramide signal amplification, and radioactive moieties. The method may then comprise detecting the presence of the label, e.g., detecting fluorescence, detecting the quantum dots, detecting bioluminescence, detecting the signal generated by the enzyme, or detecting radioactivity, respectively.

As an example, the step of detecting whether the product of double ligation is present may comprise capturing a backbone oligonucleotide of the probe on a substrate via the capture moiety, washing the substrate to remove unligated probes and retaining a captured fraction comprising the substrate and captured backbone oligonucleotide, and testing for the presence of the product of double ligation in the captured fraction. Where the product of double ligation carries a label, this may comprise testing for the presence of the label in the captured fraction. The capture moiety can be a biotin-molecule with affinity to a streptavidin substrate. Other suitable affinity tags include polyhistidine tags with affinity to immobilised metal ions, such as cobalt, nickel, copper which can be used for the purification of histidine containing sequences, e.g., backbone oligonucleotides. The capture moiety may thus be part of the sequence to be captured, e.g. a His-tag sequence, or it may be a heterogenous moiety which is not part of the nucleic acid itself.

A suitable solid substrate is a bead, for example magnetic beads to facilitate enrichment of the captured products using a magnet. The substrate may be coated with a binding member for the capture moiety, e.g. streptavidin coated magnetic beads may be used with biotinylated probes.

An advantage of some embodiments of the present method is that it do not rely on nucleic acid sequencing, nor PCR, which causes biased results because some sequences amplify more efficiently than others. Optionally though, detection may comprise a step of validating the identity of the ligated fragment by sequencing the product. One of the advantages of the present invention is that, by incorporating the actual target fragment in the product of double ligation, the product can be sequenced to confirm that the probes reacted with the correct target. This is an advantage compared with other approaches based on double ligation such as US20130172212 (Ariosa).

Multiplexing

Multiple different target nucleic acid fragments may be detected using a plurality of the probes in parallel. For example, a sample of fragmented chromosomes may be contacted with a set of probes for binding multiple fragments of a chromosome, wherein each probe in the set is for binding a different target fragment specific to that chromosome. The probes may share a common custom sequence, which can be used as a barcode to identify the probes that specifically bind that chromosome. Multiplexing can include multiplex targeting oligonucleotides and one common backbone oligonucleotide but also several sets of targeting oligonucleotides where each subset hybridises to separate backbone oligonucleotides.

Multiple probes can be used to provide a detectable signal, where the magnitude of the signal is proportional to the number of probes recognising their target fragments. Individual signals from the plurality of probes are converted into a single cumulative detectable signal, amplifying the individual signals through the multiplex probing. Ten or more probes produce a signal amplification of ten-fold or more. The generated signals depend on correctly reacted probes upon target recognition, using sequence specific hybridisation and ligation to generate the specific products of double ligation from which the signal is obtained.

Each probe that recognises its target fragment generates a ligation product, and the ligation products produced by each probe hybridisation may be individually detectable, so that an individual signal is obtainable from each. However, an elegant feature of the present invention is that these individual signals need not be individually detected, but instead are merged into a cumulative signal and the cumulative signal is detected. The cumulative signal is a combination of the individual signals and can thus be used to detect and/or quantify the ligation products, representing the presence or quantity of the nucleic acid species under investigation. Some implementations of the present method allow an earlier merging of the probe signals compared with methods involving sequencing and microarrays, in which individual signals are generated for multiple probes across a region and then the signal is merged in the analysis to represent a region. The signal can be merged before detection, so that individual signals are not separately mapped or interrogated. This enables a simpler readout format.

An individual signal may be obtainable from each product of double ligation which is formed as a result of probe hybridisation to each target fragment. So, for example, where a set of probes comprises 10 different probes that recognise 10 target fragments of a species of interest in a sample, there will be 10 ligation products including ligation junctions, and a cumulative signal may be detected, which is the combination of individual signals from the 10 ligation products. Of course, in this example the actual number of molecules probes, target fragments and ligation products may be higher than 10 because there will usually be multiple copies of each target fragment in a sample and the sample will be contacted with multiple copies of each probe.

Method of signal amplification by multiplexing can be used to detect nucleic acid species of interest in a sample, for example where a nucleic acid species is a minor or trace component in a complex nucleic acid sample. The amplification by multiplexing enables reliable detection. This may be used for example to detect microbial nucleic acid in samples, such as patient samples, for diagnostic purposes. Samples may be probed with probes specific for microbial nucleic acids of multiple species, to detect and identify those present. This is useful for detection of agents of infectious disease, such as bacteria, viruses and fungi. Specific nucleic acid transcripts may be detected. Amplification by multiplexing may also be used to quantify the nucleic acid species. By probing two or more species of nucleic acid— one or more species of interest and one or more reference nucleic acid species—the method enables quantification of the relative amounts of the two species in the sample. The method is especially useful when applied to the detection or quantification of chromosomes or chromosomal loci, for example for chromosomal copy number detection. An application of particular value is the use of such methods for identifying chromosomal defects, including for the diagnosis of cancers and congenital aneuploidies. Use for non-invasive prenatal diagnosis (NIPT) is specifically described.

A species of nucleic acid in a sample may be detected by contacting the sample with a set of probes according to the present invention, wherein each probe specifically recognises a distinct target sequence in the species of nucleic acid to be detected. The target sequences correspond to target fragments of the species of nucleic acid. Recognition of each target sequence by each probe generates a product of double ligation as described herein. A cumulative signal can then be detected, this being a combination of signals from the products. Detection of the signal indicates the presence of the species of nucleic acid in the sample. The species of nucleic acid may be quantified by quantifying the cumulative signal to determine a signal level, wherein the signal level is proportional to the quantity of the species of nucleic acid in the sample, and thereby determining the quantity of the species of nucleic acid in the sample. A first species of nucleic acid may be quantified relative to a second or reference species of nucleic acid by contacting the sample with a first set of probes and a second set of probes, wherein the probes of the first set each specifically recognise a distinct target sequence within the first species of nucleic acid and wherein the probes of the second set each specifically recognise a distinct target sequence within the second or reference species of nucleic acid. First and second cumulative signals are detected, the first cumulative signal being a combination of individual signals from products generated by probes of the first set recognising their target sequences, and the second cumulative signal being a combination of individual signals from products generated by probes of the second set recognising their target sequences. The first and second signals are quantified to determine first and second signal levels respectively, these being proportional to the quantities of the first and second species of nucleic acid in the sample. The relative quantities of the first and second nucleic acid species in the sample may thus be determined by comparing the first and second signal levels.

For example, the cumulative signal may be the summarised enumeration of clonally amplified and/or labelled products of the probes that recognise their target sequences, for example products of rolling circle amplification, or a fluorescent signal emitted from all the products where each product emits a fluorescent signal. For quantifying relative amounts of multiple species of nucleic acids, different signals are used for each species, for example products of one set of probes may emit a different wavelength or spectrum of fluorescence compared with products of another set of probes.

A species of nucleic acid in a sample may be detected in a method, comprising
contacting the sample with a set of probes, wherein each probe specifically recognises a distinct target sequence within the species of nucleic acid to be detected,
providing denaturing conditions under which the target sequences in the species of nucleic acid are single stranded,
providing conditions for annealing and ligation, under which conditions the probes hybridise to their target sequences and generate ligation products, and
detecting a cumulative signal which is a combination of individual signals from all ligation products,
wherein detection of the signal indicates the presence of the species of nucleic acid in the sample.

Details of the sample, target nucleic acid, method steps (e.g., denaturing, annealing, ligation) and probes are described elsewhere herein. The method may comprise:
(i) providing a sample in which the species of nucleic acid is fragmented into target fragments,
(ii) providing denaturing conditions under which the target fragments are single stranded
(iii) contacting the sample with a set of probes, wherein each probe specifically recognises a distinct target sequence within the species of nucleic acid to be detected, wherein the target sequences are sequences of the target fragments, and wherein each probe comprises
a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and
head and tail sequences having free 5' and 3' ends respectively, wherein the head and tail sequences are complementary to the upstream and downstream flanking sequences respectively,
(iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence
(v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, and
(vi) detecting a cumulative signal which is a combination of individual signals from all the products,
wherein detection of the signal indicates the presence of the species of nucleic acid in the sample.

The species of nucleic acid may be quantified by a method comprising
(i) providing a sample in which the species of nucleic acid is fragmented into target fragments
(ii) providing denaturing conditions under which the target fragments are single stranded
(iii) contacting the sample with a set of probes, wherein each probe specifically recognises a distinct target fragment of the species of nucleic acid to be quantified, wherein each probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence (v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, (vi) detecting a cumulative signal which is a combination of individual signals from all ligation products, and (vii) quantifying the cumulative signal to determine a signal level, wherein the signal level is proportional to the quantity of the species of nucleic acid in the sample, and thereby determining the quantity of the species of nucleic acid in the sample.

The method may be used to quantify a first species of nucleic acid relative to a second species of nucleic acid in a sample. The method may comprise:

(i) providing a sample in which the first and second species of nucleic acid are fragmented into target fragments (ii) providing denaturing conditions under which the target fragments are single stranded (iii) contacting the sample with a first set of probes and a second set of probes, wherein the probes of the first set specifically recognise distinct target fragments of the first species of nucleic acid and wherein probes of the second set specifically recognise distinct target fragments of the second species of nucleic acid, wherein each probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence (v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, (vi) detecting a first cumulative signal which is a combination of individual signals from the ligation products generated by probes of the first set, and quantifying it to determine a first signal level, wherein the first signal level is proportional to the quantity of the first species of nucleic acid in the sample, (vii) detecting a second cumulative signal which is a combination of individual signals from the ligation products generated by probes of the second set, and quantifying it to determine a second signal level, wherein the second signal level is proportional to the quantity of the second species of nucleic acid in the sample, and (viii) comparing the first and second signal levels, thereby determining the relative quantities of the first and second nucleic acid species in the sample.

Generally, the number of probes will be at least ten for each species of nucleic acid to be detected or quantified. The number of course refers to the number of different probes, rather than the absolute number of molecules of the probe. Accordingly, the nucleic acid will contain at least ten different specific target sequences, and the cumulative signal is a combination of individual signals of at least ten unique probes, this cumulative signal representing the one species of nucleic acid. High levels of multiplex can be used to obtain correspondingly high levels of signal amplification. For example, at least 100, at least 1,000, at least 10,000 or even greater numbers of probes may be used for each species of nucleic acid to be detected or quantified.

The method may comprise contacting a sample of fragmented chromosomes with multiple sets of probes for binding multiple fragments of two or more chromosomes, comprising:

a first set of probes for binding a plurality of target fragments specific to a first chromosome, and a second set of probes for binding a plurality of target fragments specific to a second chromosome, and optionally one or more further sets of probes for binding a plurality of target fragments specific to one or more further chromosomes.

Probes within a set can share a custom sequence which is common to that set and differs from the custom sequences of probes in other sets, allowing the probes from each set to be conveniently identified. Each set of probes may contain at least 500, 600, 700, 800, 900 or at least 1,000 different probes for binding a plurality of target fragments specific to the chromosome. For example, a method may use 1,000 different targeting oligonucleotides to each of chromosomes 21, 13 and 18, respectively, and three different backbone oligonucleotides, one for each chromosome subset.

It is possible to determine the relative quantities of the two or more chromosomes in a sample by detecting the products of double ligation for each set of probes and detecting the relative quantities of the custom sequences in said products.

Using probes where the targeting oligonucleotide and the upstream and downstream oligonucleotides form a circle, motifs encoding specific alleles and or loci can be incorporated in the custom sequence in high multiplex.

Digital Karyotyping and Non-Invasive Pre-Natal Diagnostics

Some embodiments of the present method can provides particular advantages in fields where precise quantification of target DNA is sought. This includes a number of nucleic acid based diagnostic techniques. One such area is the analysis of cancer DNA in a biological sample (e.g., blood)

from a patient. Another such area is non-invasive pre-natal diagnostics by analysis of cell free DNA (NIPT).

A challenge with NIPT is that a large number of specific genome fragments must be counted in order to achieve the statistical confidence required to diagnose an abnormality chromosomal aneuploidies (chromosome copy number differences). Since the foetal DNA is mixed with the maternal DNA, making up 4-30% of the genetic material in a pregnant woman's bloodstream, observing a chromosomal aneuploidy in the foetal DNA requires a very precise measurement.

The probes described herein may be used for analysing free circularising foetal DNA in samples of maternal blood. By using a plurality of probes directed to different fragments of one chromosome and a plurality of probes directed to different fragments of a second chromosome, the probes enable an imbalance in the relative number of the two chromosomes in the sample to be determined with high confidence. This allows chromosomal aneuploidies such as trisomy to be diagnosed from foetal DNA even against the high background of the maternal DNA.

Probes described herein may be used for testing maternal blood samples from pregnant women to detect foetal nucleic acid for the diagnosis of chromosomal abnormalities such as trisomy, testing patient samples for tumour DNA for the diagnosis or monitoring of the presence of a tumour in the patient. Other uses include testing samples of material for the presence of microbial nucleic acid, where detection of the microbial nucleic acid indicates infection of the material by the microbe, which may be an infectious agent such as a bacterium, virus or fungus. The sample may be a tissue or blood sample from a patient.

More generally, by using hundreds or thousands of different probes, the present method can achieve high precision by detecting hundreds or thousands of specific nucleic acid fragments, providing advantages across a range of diagnostic applications. Detecting a multitude of DNA fragments from the chromosome or chromosomal loci associated with a particular disease enables the amount of that chromosome or locus to be measured relative to a control chromosome or locus, so that even slight differences in a sample can be confidently detected.

By analysing short target fragments a large proportion of the highly fragmented cell free DNA in maternal blood can be analysed with high efficiency. This is important since very low amounts of cell free DNA are available in maternal blood.

A method of quantifying a first chromosome or chromosomal locus relative to a second chromosome or chromosomal locus in a sample of nucleic acid obtained from an individual may comprise (i) providing a sample in which the first and second chromosomes or chromosomal loci are fragmented into target fragments (ii) providing denaturing conditions under which the target fragments are single stranded (iii) contacting the sample with a first set of probes and a second set of probes, wherein the probes of the first set specifically recognise distinct target fragments of the first chromosome and wherein probes of the second set specifically recognise distinct target fragments of the second chromosome, wherein each probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and head and tail sequences having free 5' and 3' ends respectively, wherein the head and tail sequences are complementary to the upstream and downstream flanking sequences respectively, (iv) providing annealing conditions under which the head and tail sequences hybridise to the flanking sequences, and target fragments, if present, hybridise to the target-complementary sequence of the probes, thereby positioning the ends of the target fragment in juxtaposition with the 5' end of the head sequence and the 3' end of the tail sequence (v) providing conditions for ligation so that, if a target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, (vi) detecting a first cumulative signal which is a combination of individual signals from the ligation products generated by probes of the first set, and quantifying it to determine a first signal level, wherein the first signal level is proportional to the quantity of the first chromosome or chromosomal locus in the sample, (vii) detecting a second cumulative signal which is a combination of individual signals from the ligation products generated by probes of the second set, and quantifying it to determine a second signal level, wherein the second signal level is proportional to the quantity of the second chromosome or chromosomal locus in the sample, and (viii) comparing the first and second signal levels, thereby determining the relative quantities of the first and second chromosomes or chromosomal loci in the sample.

The method may be used for diagnosing aneuploidy (e.g. trisomy) in a foetus, where the sample of nucleic acid is a sample obtained from maternal blood and contains cell free foetal DNA mixed with maternal DNA, and wherein an unequal ratio of the first and second signal levels is indicative of aneuploidy (e.g. trisomy).

Probes

Further aspects include probes suitable for use in the present method. Examples of probes and their features have already been described above. Some further features and examples are described here.

The probe nucleic acid is preferably DNA. However, it may be another nucleic acid, naturally occurring or not. The standard bases of DNA are A, T, C and G, but probe nucleic acid may optionally include non-standard nucleotides.

In general, a probe according to the present invention comprises a targeting oligonucleotide and head and tail sequences. The head and tail sequences may be part of the targeting oligonucleotide, or one or both of them may be on a different nucleic acid molecule. Optionally, the probe comprises the targeting oligonucleotide, a backbone oligonucleotide comprising the head sequence and a backbone oligonucleotide comprising the tail sequence. A probe therefore may comprises one, two or three nucleic acid molecules in its non-ligated form.

The targeting oligonucleotide is longer than the target fragment and contains an internal target-complementary sequence, so that hybridisation between the targeting oligonucleotide and the target fragment forms a double stranded sequence located between upstream and downstream flanking sequences of the targeting oligonucleotide. The head and tail sequences have free 5' and 3' ends respectively, and are complementary to the upstream and downstream flanking sequences respectively. Under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences.

The probes may be designed so that hybridisation of the target fragment in the gap completes a circle of nucleic acid, the circle comprising the target fragment and the head and tail sequences.

The head and/or tail sequence of the probe is preferably joined to a custom sequence which is not complementary to other regions of the probe or to the target fragment.

In some embodiments of the probe, a single nucleic acid molecule comprises the head and tail sequences.

The head and tail sequences may be separate from the targeting oligonucleotide so that they bind in trans to the flanking sequences. For example, the head and tail sequences may be at 5' and 3' ends respectively of a backbone oligonucleotide. A custom sequence can be included between the head and tail sequences of the backbone oligonucleotide. An example of such a probe is shown in FIG. 1 and FIG. 3. Alternatively, the head and tail sequences of the backbone oligonucleotide may be adjacent, with no intervening nucleotide sequence. In such a case, the flanking sequences of the targeting oligonucleotide hybridise along the full length of the backbone oligonucleotide and may circularise it.

The probes may be designed so that the head sequence is a 5' end of the targeting oligonucleotide and/or the tail sequence is a 3' end of the targeting oligonucleotide, so that hybridisation of the target fragment in the gap completes a strand of nucleic acid comprising the target fragment, the head and tail sequences, the target complementary sequence and the flanking sequences. The head and tail sequences may be at ends of the targeting oligonucleotide and bind in cis to the flanking sequences. An example of such a probe is shown in FIG. 4. In this version of the probe, the head and tail sequences and the target complementary sequence all become circularised with the target fragment. Custom sequences can be positioned in the loops of the oligonucleotide. The probe nucleic acid is relatively long but has the advantage of joining the oligonucleotide structure into one molecule that is pre-assembled and does not require hybridisation of different probe nucleic acid molecules.

Probes can also be designed with a backbone oligonucleotide, which is a separate molecule of nucleic acid from the targeting oligonucleotide. The tail sequence can be a 3' end of the targeting oligonucleotide and the head sequence a 5' end of a backbone oligonucleotide. Alternatively the head sequence can be a 5' end of the targeting oligonucleotide and the tail sequence a 3' end of a backbone oligonucleotide. A custom sequence can be introduced in the targeting oligonucleotide, for example to provide a loop between the head or tail sequence and the flanking sequence. An advantage with using this probe approach is that a detection sequence can be introduced in the loop and is associated with the target complementary sequence, which can be advantageous for multiplex methods, especially higher multiplexes with high-plex detection schemes. The backbone oligonucleotide can further comprise a custom sequence. By providing the probe in two oligonucleotides, the probe nucleic acid molecules are shorter than the single oligonucleotide version but maintain the same function.

Another design of the probe provides the head and tail sequences on two backbone oligonucleotides. Thus, the probe comprises a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, a backbone oligonucleotide comprising a head sequence having a free 5' end, and a backbone oligonucleotide comprising a tail sequence having a free 3' end, wherein the head and tail oligonucleotide sequences are complementary to the upstream and downstream flanking sequences respectively.

One backbone oligonucleotide may carry a capture moiety, in which case the other backbone oligonucleotide is used for detection and may carry a heterogeneous label. One or both backbone oligonucleotides may further comprise a custom sequence. Alternatively or additionally, the targeting oligonucleotide may include a custom sequence.

Under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences. Hybridisation of the target fragment in the gap completes a strand of nucleic acid comprising the target fragment and the head and tail sequences. The strand carries the capture moiety and the label, permitting detection using the capture/detect methods described elsewhere herein.

Kits and Sets of Probes

A further aspect of this disclosure is set of probes for binding single stranded target nucleic acid fragments, comprising a plurality of probes, the probes having a plurality of different target-complementary sequences for the binding multiple different target fragments.

The set of probes may be for binding multiple fragments of a human chromosome, wherein each probe in the set is for binding a different target fragment specific to that chromosome. Such probes may all include a common custom sequence, as part of the targeting oligonucleotide or as part of a backbone oligonucleotide.

Multiple sets of probes can be provided for binding different fragments of two or more human chromosomes, comprising:

a first set of probes for binding a plurality of target fragments specific to a first chromosome, and a second set of probes for binding a plurality of target fragments specific to a second chromosome, and optionally one or more further sets of probes for binding a plurality of target fragments specific to one or more further chromosomes. The probes within a set can share a custom sequence which is common to that set and differs from the custom sequences of probes in other sets.

Kits can also be provided, comprising sets of probes in solution in one or more containers.

Uses

The probes, sets of probes and kits described herein may be used for testing samples for the presence of target nucleic acid fragments. They may be used for identifying the presence of a defined target fragment in a sample of fragmented nucleic acid in vitro.

One aspect includes the use of a probe for testing a sample for the presence of a target single stranded nucleic acid fragment, wherein the probe comprises a targeting oligonucleotide containing a sequence which is the exact complement of the target fragment, and head and tail oligonucleotide sequences which hybridise adjacent to the target fragment on the targeting oligonucleotide, wherein hybridisation between the target fragment and the probe templates the target fragment for ligation to the head and tail sequences.

Examples of such probes and of their use in methods of testing samples are described in more detail elsewhere herein. Uses include testing maternal blood samples from pregnant women to detect foetal nucleic acid for the diagnosis of chromosomal abnormalities such as trisomy, and testing patient samples for tumour DNA for the diagnosis or monitoring of the presence of a tumour in the patient. Other uses include testing samples of material for the presence of microbial nucleic acid, where detection of the microbial nucleic acid indicates infection of the material by the microbe, which may be an infectious agent such as a bacterium, virus or fungus. The sample may be a tissue or blood sample from a patient.

EXAMPLES

The following example is provided in order to demonstrate and further illustrate certain embodiments and aspects of the present invention and are not to be construed as limiting the scope thereof.

Example 1

A protocol suitable for performing the method illustrated in FIG. 1 is as follows: 1) 10 ng of DNA is digested with 1 unit of restriction enzyme in corresponding compatible restriction enzyme buffer. The reaction is incubated in 37 C for 1 h, followed by enzymatic deactivation at 80 C for 20 min. 2) The DNA fragments are denatured to single stranded fragments at 95 C for 10 min and mixed with probes and ligase to form circles. The probe pool are added in 10 pM individual concentration along with 1 U of Ampligase (Epicentre) and incubated at 55 C for 1 h in ligase buffer. 3) 1 U Exonuclease is added to remove non-reacted probes and fragments. I U of Lambda exonuclease (Epicentre) is added at 37 C for 1 h in corresponding exonuclease buffer followed by enzyme inactivation at 80 C for 20 min. 4) The remaining circles are amplified by RCA. 1 U of phi29 polymerase (New England Biolabs) is added in corresponding phi29 buffer and nucleotides (dNTPs) at 37 C for 1 h.

Example 2

Figure 2:
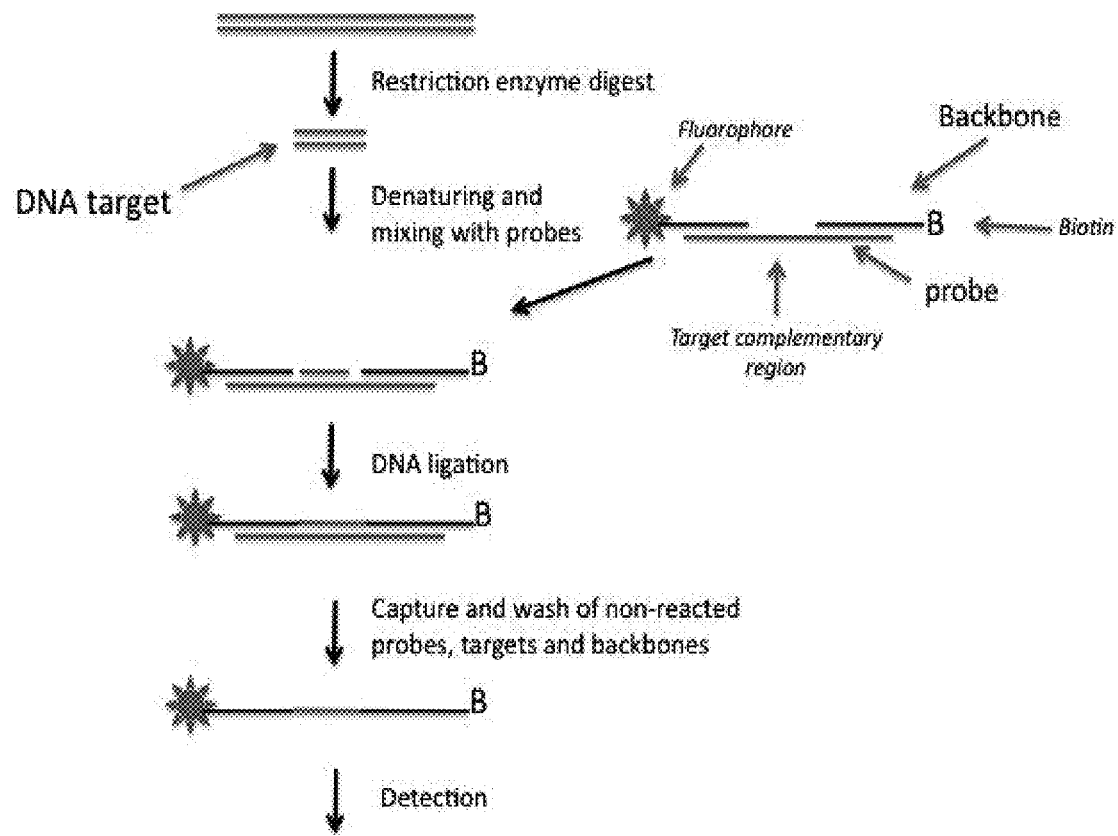
FIG. 2 schematically illustrates one embodiment of the subject method in which a linear ligation product is formed and enriched with solid-phase reagents.

A protocol suitable for performing the method illustrated in FIG. 2 is as follows: 1) 10 ng of DNA is digested with 1 unit of restriction enzyme in corresponding compatible restriction enzyme buffer. The reaction is incubated in 37 C for 1 h, followed by enzymatic deactivation at 80 C for 20 min. 2) The DNA fragments are denatured to single stranded fragments at 95 C for 10 min and mixed with probes and ligase to form linear ligation products. The probe pool are added in 10 pM individual concentration along with 1 U of Ampligase (Epicentre) and incubated at 55 C for 1 h in ligase buffer. 3) The ligation product is captured on magnetic streptavidin beads. To remove non-reacted probes and fragments, the solution is mixed with 10 ml M-280 streptavidin coated magnetic beads (Invitrogen) in Tris-HCl (pH 7.5), 3.5 mM EDTA and 0.07% Tween-20 in a final volume of 200 ml, and incubated at room temperature for 15 min. After incubation, the beads are collected using a ring magnet and supernatant removed.

Example 3

Materials and Methods

Sample Preparation:

10 ml blood was collected from each subject into a cell-free DNA tube (Streck, Omaha, Nebr.). Plasma was isolated from blood by a double centrifugation protocol (1600 g for 10 min, followed by 16 000 g for 10 min, after a tube transfer following the first spin). cfDNA was isolated by the Qiagen ccf nucleic acid kit (Qiagen, Hilden, Germany) according to the manufacturer's protocol. The resulting DNA was eluted in 50 ul of buffer (part of the Qiagen kit).

Probe and Backbone Design:

The multiplexed probe technology herein described enables specific and simultaneous amplification of thousands of chromosomal fragments. Probes were designed to capture 2500-5000 fragments (targets) from each of chromosomes 21, 18, and 13. Targets were selected to have unique sequence in the genome, uniformed AT/GC composition, not include known polymorphism nor CNVs in target sequence, and a size between 18-35 bp. Probes targeting 2500 fragments from each chromosome 13 and 18 were pooled together with 5000 probes targeting fragments from chromosome 21 to create a single oligo probe pool.

Example sequence of probes, "N" represents target complementary sequence:

```
                                            (SEQ ID NO: 1)
ATGTGACCCTTCCGTCTGTTGAGTTAGGCCNNNNNNNNNNNNNNNNNNNNNN
NNNNNNNNNNNTCGTGCCTTGTCATTCGGGAGCACTAACTGCTG
```

The backbones, with head and tail sequences complementary to the ends of the probe, were designed to include sequence motifs for both sequencing and digital counting. Two backbones were used in the experiments outlined in the result section; one complementary to probes targeting chromosome 13 and 18: (/5Phos/CGCACACGATTAAGGTC-CAGTCACAGGCAGAGATCGGAAGAGCGTCGTG-TAGGG AAAGAGTGTNNNNNNNNNNGTGTAGATCTCGGTG-GTCGCCGTATCATTTCATGCTGCTAAC GGTC-GAGTCGGACAGGTGGCTCCACTAAATAGACGCA); SEQ ID NO:2, and one backbone targeting chromosome 21:

```
(/5Phos/GGCCTAACTCAACAGACGGAAGGGTCACATAGATCGGAAGAG

CGTCGTGTAGGGAAAGAGTGTNNNNNNNNNNGTGTAGATCTCGGTGGTCG

CCGTATCATTTCATGCTGCTAACGGTCGAGCAGTTAGTGCTCCCGAATGA

CAAGGCACGA; SEQ ID NO: 3).
```

Biochemistry Probe Protocol:

50 ul of purified cfDNA was digested with 5 U of MseI (New England Biolabs) in 1×NEB4 buffer (New England Biolabs) and 1×BSA in a total volume of 55 ul at 37 C in 30 min followed by heat inactivation at 65 C in 20 min. The digested DNA was then mix with ligation mix along with probes and backbones. The 55 ul of digested DNA was mixed with probes (1 pM/probe), backbones (60 nM each), 1× ligation buffer (Epicentre), 100 U of Ampligase (Epicentre), 1 mM NAD, and 5 mM Mg$^{2+}$ to a total volume of 70 ul. The digested fragments were first denatured to single stranded DNA at 95 C in 5 min followed by 55 C hybridization and ligation in 16 h. The ligation mix was then treated with exonucleases to remove any remaining linear DNA molecules. The ligation reaction was mixed with 20 U of ExoI (NEB) and 5 U of ExoIII (NEB) and 1×BSA tot total volume of 75 ul at 37 C for 60 min followed by heat inactivation at 65 C for 10 min.

Analysis:

For sequencing analysis, the exo treated circles was amplified with sequencing primers complementary to the Illumina sequencing instrument and subsequently loaded on the Illumina Miseq instrument according to manufacturers protocol.

For digital analysis, the exo treated reactions was subjected to a rolling circle amplification reaction (RCA) to generate discrete DNA objects of concatemeric copies of the circle. 37.5 ul of exo treated circles were mixed with 4 mM DTT, 3 U of phi29 polymerase (NEB), 0.1 uM primer, 1 mM dNTP mix (NEB) and 1×BSA in a total volume in 50 ul, and incubated at 37 C for 1 h followed by a heat inactivation at 65 C for 10 min. The RCA reaction was then labeled with fluorescently labeled oligonucleotides complementary to the backbone sequence. 50 ul of RCA products was mixed with 0.1% Tween 20 (Sigma), 5 nM labeled oligonucleotides, and 2×SSC (Sigma) in a total volume of 100 ul. The labeled RCA-products were finally deposited on a microscope slide coated with Poly-lysine (Sigma) and counted in a fluorescent microscope.

Results

The probe method herein described was demonstrated on Illumina sequencing and a digital counting system. To demonstrate the performance of the probe method, a DNA sample with trisomy 21 was mixed with DNA extracted from normal plasma samples (3-5 ml plasma) in different concentrations. The samples was then carried through the probe method and evaluated by sequencing.

Figure 8:
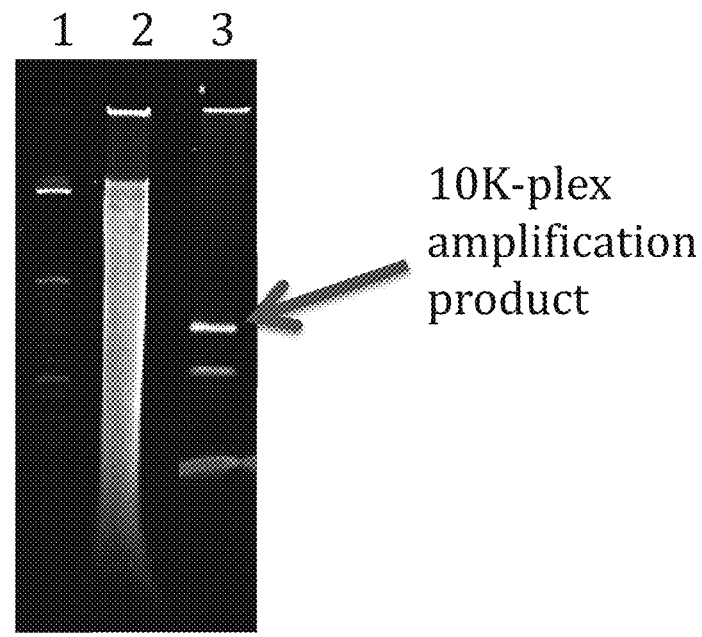
FIG. 8 is an image of a gel showing the specificity of the method described herein.

For the results shown in FIG. 8, 100 ng of cell line DNA was subjected to the protocol described above. 10,000 probes were mixed in a pool to specifically circularize 10,000 corresponding chromosomal fragments from chromosome 13, 18, and 21. The 10,000 resulting circles were then amplified with Illumina-corresponding PCR primers and analyzed on gel prior sequencing. Lane 1 corresponds to DNA ladder, lane 2 the DNA sample after digestion, and lane 3 the PCR product with 10,000 amplified fragments.

Figure 9:
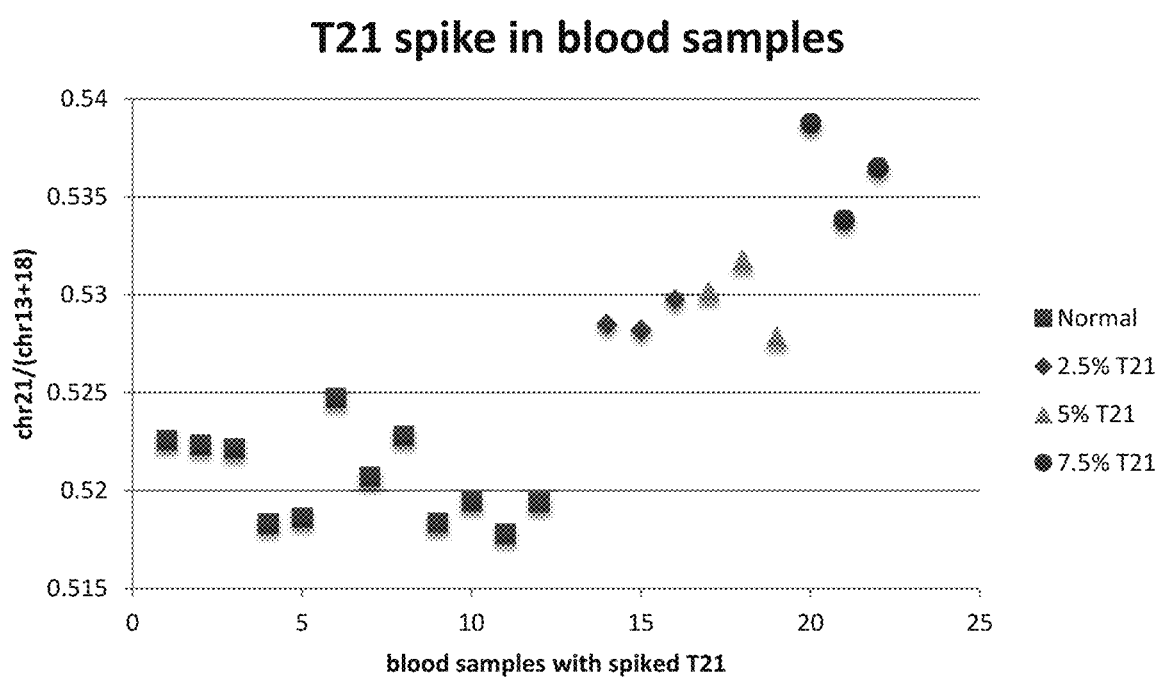
FIG. 9 is a graph showing the precision of the method described herein.

For the results shown in FIG. 9, 12 normal plasma samples were analyzed in parallel with samples carry DNA with trisomy 21 in different concentrations. DNA were extracted and processed through the 10 K-plex probe protocol and finally sequenced on Illumina sequencer. Using a confidence interval providing 99% specificity, the positive samples are detected with a 90% sensitivity based on the estimated normal distributions.

Figure 10:
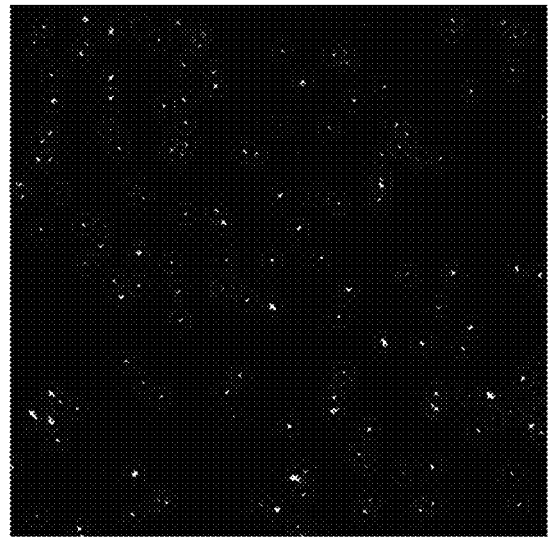
FIG. 10 panel A shows an image of labeled RCA products on the surface of a slide; panel B shows how ratios of fragments from different chromosomes can be accurately determined by counting individual RCA products.
Figure 10:
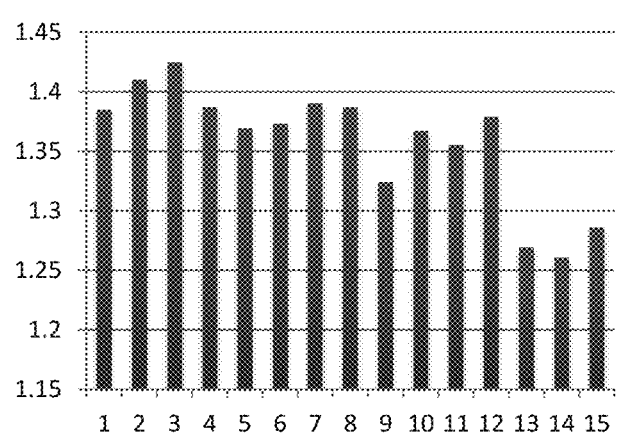

To demonstrate the principle of converting targeted fragments to labeled DNA objects, 10% of DNA with trisomy 21 was added to 20 ng normal cell line DNA and carried through the probe method. The resulting labeled RCA-products were randomly deposited on a microscope slide and counted. Probes targeting fragments derived from chromosome 21 was labeled with one color and fragments derived from Chr. 13 and 18 with a reference color. These results are shown in FIG. 10. Panel (A) of FIG. 10 shows an image from a microscope, showing labeled and detected RCA-products. By labeling all fragments from chromosome 13 with one fluorophore and fragments from a reference chromosome with a second fluorophore, a ratio measurement can be achieve. Panel (B): 20 ng of DNA processed through the 10 K-plex probe protocol and converted to labeled RCA-products. The RCA-products were analyzed in parallel with samples carry a 10% addition of trisomy 21 DNA. 12 normal DNA samples (sample #1-12) were analyzed in parallel with three positive samples (sample #13-15).

Further Description

The following clauses are part of the description.

1. A method of testing a sample for the presence of a target nucleic acid fragment, comprising
   (i) providing a sample of fragmented nucleic acid
   (ii) providing denaturing conditions under which the target fragment is single stranded
   (iii) contacting the sample with a nucleic acid probe comprising
       a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and
       head and tail sequences having free 5' and 3' ends respectively, wherein the head and tail sequences are complementary to the upstream and downstream flanking sequences respectively,
   (iv) providing annealing conditions under which the head and tail sequences hybridise to the flanking sequences, and the target fragment, if present, hybridises to the target-complementary sequence, thereby positioning the ends of the target fragment in juxtaposition with the 5' end of the head sequence and the 3' end of the tail sequence
   (v) providing conditions for ligation so that, if the target fragment is present, the 3' end of the target fragment is ligated to the 5' end of the head sequence to form a first ligation junction, and the 5' end of the target fragment is ligated to the 3' end of the tail sequence to form a second ligation junction, producing a product of double ligation comprising a continuous strand of nucleic acid comprising the head and tail sequences and the target fragment, and
   (vi) detecting whether the product of double ligation is present,
   wherein detecting the product of double ligation indicates the presence of the target fragment in the sample.

2. A method according to clause 1, wherein the sample of fragmented nucleic acid is a restriction enzyme digest and the target fragment is a restriction fragment.

3. A method according to clause 1 or clause 2, wherein the 5' end of the head sequence and the 3' end of the target fragment hybridise to adjacent nucleotides of the targeting oligonucleotide, and the 3' end of the tail sequence and the 5' end of the target fragment hybridise to adjacent nucleotides of the targeting oligonucleotide.

4. A method according to any of the preceding clauses, wherein the step of detecting the product of double ligation comprises providing conditions for amplification across the first and second ligation junctions of the continuous strand of nucleic acid, and detecting whether an amplification product is present.
5. A method according to any of the preceding clauses, wherein the continuous strand of nucleic acid comprising the head and tail sequences and the target fragment is a circle of nucleic acid.
6. A method according to clause 5, wherein the step of detecting the product of double ligation comprises providing conditions for rolling circle replication and detecting whether a product of rolling circle replication is present.
7. A method according to clause 6, wherein the rolling circle replication is hyper branched rolling circle replication.
8. A method according to any of clauses 5 to 7, wherein the probe comprises the head and tail sequences on one nucleic acid molecule.
9. A method according to clause 8, wherein the probe comprises a backbone oligonucleotide having the head and tail sequences at its 5' end 3' ends respectively, wherein the head and tail sequences of the backbone oligonucleotide bind in trans to the flanking sequences of the targeting oligonucleotide under the annealing conditions.
10. A method according to clause 9, wherein the backbone oligonucleotide comprises a custom sequence between the head and tail sequences, wherein the custom sequence is not complementary to other regions of the probe or to the target fragment.
11. A method according to clause 9, wherein the head and tail sequences of the backbone oligonucleotide are adjacent.
12. A method according to any of clauses 5 to 8, wherein the head and tail sequences are at ends of the targeting oligonucleotide and bind in cis to the flanking sequences under the annealing conditions.
13. A method according to clause 12, wherein the targeting oligonucleotide comprises a custom sequence between the targeting oligonucleotide and the head and/or tail sequence, wherein the custom sequence is not complementary to other regions of the probe or to the target fragment.
14. A method according to any of clauses 1 to 7, wherein the tail sequence is at the 3' end of the targeting oligonucleotide, and the probe comprises a backbone oligonucleotide having the head sequence at its 5' end,
wherein under the annealing conditions the tail sequence binds in cis to the downstream flanking sequence of the targeting oligonucleotide, and the head sequence of the backbone oligonucleotide binds in trans to the upstream flanking sequence of the targeting oligonucleotide.
15. A method according to clause 14, wherein the backbone oligonucleotide comprises a pair of inverted repeat sequences, wherein
under the annealing conditions the inverted repeat sequences form a hairpin structure, thereby positioning the 3' end of the backbone oligonucleotide in juxtaposition with the 5' end of the targeting oligonucleotide, and wherein
under the conditions for ligation, the 5' end of the targeting oligonucleotide is ligated to the 3' end of the backbone oligonucleotide, so that the product of double ligation is a circle of nucleic acid comprising the targeting oligonucleotide, the target fragment and the backbone oligonucleotide.
16. A method according to any of clauses 1 to 7, wherein the head sequence is at the 5' end of the targeting oligonucleotide, and the probe comprises a backbone oligonucleotide having the tail sequence at its 3' end,
wherein under the annealing conditions the head sequence binds in cis to the upstream flanking sequence of the targeting oligonucleotide, and the tail sequence of the backbone oligonucleotide binds in trans to the downstream flanking sequence of the targeting oligonucleotide.
17. A method according to clause 16, wherein the backbone oligonucleotide comprises a pair of inverted repeat sequences, wherein
under the annealing conditions the inverted repeat sequences form a hairpin structure, thereby positioning the 5' end of the backbone oligonucleotide in juxtaposition with the 3' end of the targeting oligonucleotide, and wherein
under the conditions for ligation, the 3' end of the targeting oligonucleotide is ligated to the 5' end of the backbone oligonucleotide, so that the product of double ligation is a circle of nucleic acid comprising the targeting oligonucleotide, the target fragment and the backbone oligonucleotide.
18. A method according to any of clauses 14 to 17, wherein the backbone oligonucleotide comprises a custom sequence between the inverted repeat sequence, so that under the annealing conditions the backbone oligonucleotide forms a hairpin loop.
19. A method according to any of clauses 1 to 4, wherein the continuous strand of nucleic acid comprising the head and tail sequences and the target fragment is a linear strand of nucleic acid.
20. A method according to clause 19, wherein the tail sequence is at the 3' end of the targeting oligonucleotide, and the probe comprises a backbone oligonucleotide having the head sequence at its 5' end,
wherein under the annealing conditions the tail sequence binds in cis to the downstream flanking sequence of the targeting oligonucleotide, and the head sequence of the backbone oligonucleotide binds in trans to the upstream flanking sequence of the targeting oligonucleotide.
21. A method according to any of clauses 14, 15 or 20, wherein the targeting oligonucleotide comprises a custom sequence between the downstream flanking sequence and the tail sequence, so that under the annealing conditions the targeting oligonucleotide forms a hairpin loop.
22. A method according clause 19, wherein the head sequence is at the 5' end of the targeting oligonucleotide, and the probe comprises a backbone oligonucleotide having the tail sequence at its 3' end,
wherein under the annealing conditions the head sequence binds in cis to the upstream flanking sequence of the targeting oligonucleotide, and the tail sequence of the backbone oligonucleotide binds in trans to the downstream flanking sequence of the targeting oligonucleotide.
23. A method according to any of clauses 16, 17 or 22, wherein the targeting oligonucleotide comprises a custom sequence between the head sequence and the upstream flanking sequence, so that under the annealing conditions the targeting oligonucleotide forms a hairpin loop.
24. A method according to any of clauses 14 to 18 or 20 to 23, wherein the backbone oligonucleotide carries a capture moiety.
25. A method according to clause 19, wherein the probe comprises a backbone oligonucleotide comprising a head sequence having a free 5' end, and a backbone oligonucleotide comprising a tail sequence having a free 3' end, wherein under the annealing conditions the head and tail sequences bind in trans to the flanking sequences of the targeting oligonucleotide.
26. A method according to clause 25, wherein one or both backbone oligonucleotides further comprise a custom sequence, wherein the custom sequence is not complementary to other regions of the probe or to the target fragment.
27. A method according to clause 25 or clause 26, wherein one of the backbone oligonucleotides carries a capture moiety.
28. A method according to clause 27, wherein the other backbone oligonucleotide carries a heterogeneous label.
29. A method according to clause 28, wherein the label is a fluorophore.
30. A method according to clause 24 or any of clauses 27 to 29, wherein the step of detecting whether the product of double ligation is present comprises capturing the backbone oligonucleotide on a substrate via the capture moiety, washing the substrate to remove unligated probes and retaining a captured fraction comprising the substrate and captured backbone oligonucleotide, and testing for the presence of the product of double ligation in the captured fraction.
31. A method according to clause 28 or clause 29, wherein the step of detecting whether the product of double ligation is present comprises capturing the backbone oligonucleotide on a substrate via the capture moiety, washing the substrate to remove unligated probes and retaining a captured fraction comprising the substrate and captured backbone oligonucleotide, and testing for the presence of the label in the captured fraction.
32. A method according to clause 24 or any of clauses 27 to 31, wherein the capture moiety is biotin.
33. A method according to any of the preceding clauses, wherein the target-complementary sequence has a length of 10 to 30 nucleotides.
34. A method according to any of the preceding clauses, wherein the target-complementary sequence has fewer than 5 base pair mismatches with the target fragment.
35. A method according to clause 34, wherein the target-complementary sequence is the exact complement of the target fragment.
36. A method according to any of the preceding clauses, wherein the flanking sequences each have a length of 10 to 30 nucleotides.
37. A method according to any of the preceding clauses, wherein the upstream and downstream flanking sequences are different from each other.
38. A method according to any of the preceding clauses, wherein the head sequence has fewer than 5 base pair mismatches with the upstream flanking sequence and the tail sequence has fewer than 5 base pair mismatches with the downstream flanking sequence.
39. A method according to clause 38, wherein the head sequence is the exact complement of the upstream flanking sequence and the tail sequence is the exact complement of the downstream flanking sequence.
40. A method according to any of the preceding clauses, wherein the targeting oligonucleotide is linear.
41. A method according to any of the preceding clauses, wherein the sample is a sample of fragmented human chromosomes and the target fragment is a human genome fragment specific to one chromosome.
42. A method according to clause 41, wherein the target fragment is specific to one locus of the human genome.
43. A method according to any of the preceding clauses, wherein the probe nucleic acid is DNA.
44. A method according to any of the preceding clauses, wherein the method comprises multiplex testing for multiple different target nucleic acid fragments using a plurality of the probes in parallel.
45. A method according to clause 44, wherein the method comprises contacting a sample of fragmented chromosomes with a set of probes for binding multiple fragments of a chromosome, wherein each probe in the set is for binding a different target fragment specific to that chromosome.
46. A method according to clause 45, wherein the probes share a common custom sequence.
47. A method according to clause 44, wherein the method comprises contacting a sample of fragmented chromosomes with sets of probes for binding multiple fragments of two or more chromosomes, wherein the sets of probes comprise:
a first set of probes for binding a plurality of target fragments specific to a first chromosome, and
a second set of probes for binding a plurality of target fragments specific to a second chromosome, and optionally one or more further sets of probes for binding a plurality of target fragments specific to one or more further chromosomes.
48. A method according to clause 47, wherein each set of probes comprises at least 500 different probes for binding a plurality of target fragments specific to the chromosome.
49. A method according to clause 47 or clause 48, wherein the probes within a set share a custom sequence which is common to that subset and differs from the custom sequences of probes in other sets.
50. A method according to clause 49, comprising determining the relative quantities of the two or more chromosomes in the sample by detecting the products of double ligation for each set of probes and detecting the relative quantities of the custom sequences in said products.
51. A method according to any of clauses 45 to 50, wherein the chromosome or chromosomes are human.
52. A nucleic acid probe for binding a single stranded target nucleic acid fragment, wherein the probe comprises
a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and
head and tail sequences having free 5' and 3' ends respectively, wherein the head and tail sequences are complementary to the upstream and downstream flanking sequences respectively
so that under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences, and wherein
hybridisation of the target fragment in the gap completes a circle of nucleic acid, the circle comprising the target fragment and the head and tail sequences.
53. A nucleic acid probe according to clause 52, wherein the head and/or tail sequence is joined to a custom sequence, wherein the custom sequence is not complementary to other regions of the probe or to the target fragment.
54. A nucleic acid probe according to clause 52 or clause 53, wherein a single nucleic acid molecule comprises the head and tail sequences.

55. A probe according to clause 52 or clause 53, wherein the head and tail sequences are separate from the targeting oligonucleotide and bind in trans to the flanking sequences.
56. A probe according to clause 55, wherein the head and tail sequences are at 5' and 3' ends respectively of a backbone oligonucleotide.
57. A probe according to clause 56, wherein the backbone oligonucleotide comprises a custom sequence between the head and tail sequences, wherein the custom sequence is not complementary to other regions of the probe or to the target fragment.
58. A probe according to clause 56, wherein the head and tail sequences of the backbone oligonucleotide are adjacent.
59. A nucleic acid probe for binding a single stranded target nucleic acid fragment, wherein the probe comprises
a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide, and
head and tail sequences having free 5' and 3' ends respectively, wherein the head and tail oligonucleotide sequences are complementary to the upstream and downstream flanking sequences respectively
so that under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences, and wherein
the head sequence is a 5' end of the targeting oligonucleotide and/or the tail sequence is a 3' end of the targeting oligonucleotide, so that hybridisation of the target fragment in the gap completes a strand of nucleic acid comprising the target fragment, the head and tail sequences, the target complementary sequence and the flanking sequences.
60. A probe according to clause 52 or clause 59, wherein the head and tail sequences are at ends of the targeting oligonucleotide and bind in cis to the flanking sequences.
61. A probe according to clause 52 or clause 59, wherein the tail sequence is a 3' end of the targeting oligonucleotide and the head sequence is a 5' end of a backbone oligonucleotide separate from the targeting oligonucleotide.
62. A probe according to clause 52 or clause 59, wherein the head sequence is a 5' end of the targeting oligonucleotide and the tail sequence is a 3' end of a backbone oligonucleotide separate from the targeting oligonucleotide.
63. A probe according to clause 61 or clause 62, wherein the backbone oligonucleotide further comprises a custom sequence, wherein the custom sequence is not complementary to other regions of the probe or to the target fragment.
64. A nucleic acid probe for binding a single stranded target nucleic acid fragment, wherein the probe comprises
a targeting oligonucleotide which is longer than the target fragment and contains an internal target-complementary sequence, so that hybridisation between the targeting oligonucleotide and the target fragment forms a double stranded sequence located between upstream and downstream flanking sequences of the targeting oligonucleotide,
a backbone oligonucleotide comprising a head sequence having a free 5' end, and
a backbone oligonucleotide comprising a tail sequence having a free 3' end,
wherein the head and tail oligonucleotide sequences are complementary to the upstream and downstream flanking sequences respectively, and wherein
one backbone oligonucleotide carries a capture moiety and the other backbone oligonucleotide carries a heterogeneous label,
so that under annealing conditions in the presence of the target fragment, the head and tail sequences hybridise to the flanking sequences, defining a gap between the 5' end of the head sequence and the 3' end of the tail sequence, wherein the target fragment hybridises to the target-complementary sequence in the gap, thereby positioning the ends of the target fragment in juxtaposition with the 5' end of the head sequence and the 3' end of the tail sequences, and wherein
hybridisation of the target fragment in the gap completes a strand of nucleic acid comprising the target fragment and the head and tail sequences, wherein the strand carries the capture moiety and the label.
65. A probe according to clause 64, wherein the capture moiety is biotin.
66. A probe according to clause 64 or clause 65, wherein the label is a fluorophore.
67. A probe according to any of clauses 64 to 66, wherein one or both backbone oligonucleotides further comprise a custom sequence, wherein the custom sequence is not complementary to other regions of the probe or to the target fragment.
68. A probe according to any of clauses 52 to 67, wherein the targeting oligonucleotide further comprises a custom sequence which is not complementary to other regions of the probe or to the target fragment.
69. A probe according to any of the preceding clauses, wherein the target-complementary sequence has a length of 10 to 30 nucleotides.
70. A probe according to any of the preceding clauses, wherein the target-complementary sequence has fewer than 5 base pair mismatches with the target fragment.
71. A probe according to clause 70, wherein the target-complementary sequence is the exact complement of the target fragment.
72. A probe according to any of clauses 52 to 71, wherein the flanking sequences each have a length of 10 to 30 nucleotides.
73. A probe according to any of clauses 52 to 72, wherein the upstream and downstream flanking sequences of the targeting oligonucleotide are different from each other.
74. A probe according to any of clauses 52 to 73, wherein the head sequence has fewer than 5 base pair mismatches with the upstream flanking sequence and the tail sequence has fewer than 5 base pair mismatches with the downstream flanking sequence.
75. A probe according to clause 74, wherein the head and tail sequences are the exact complement of the flanking sequences.
76. A probe according to any of clauses 52 to 75, wherein the targeting oligonucleotide is linear.
77. A probe according to any of clauses 52 to 76, wherein the target fragment is a restriction endonuclease fragment.
78. A probe according to any of clauses 52 to 77, wherein the target fragment is a human genome fragment.
79. A probe according to clause 78, wherein the target fragment is a human genome fragment specific to one chromosome.
80. A probe according to clause 79, wherein the target fragment is specific to one locus of the human genome.

81. A probe according to any of clauses 52 to 80, wherein the probe nucleic acid is DNA.
82. A set of probes for binding single stranded target nucleic acid fragments, comprising a plurality of probes according to any of clauses 52 to 81, the probes having a plurality of different target-complementary sequences for the binding multiple different target fragments.
83. A set of probes according to clause 82 which is for binding multiple fragments of a human chromosome, wherein each probe in the set is for binding a different target fragment specific to that chromosome.
84. A set of probes according to clause 83, wherein the probes share a common custom sequence.
85. Sets of probes for binding different fragments of two or more human chromosomes, comprising:
a first set of probes for binding a plurality of target fragments specific to a first chromosome, and
a second set of probes for binding a plurality of target fragments specific to a second chromosome, and optionally one or more further sets of probes for binding a plurality of target fragments specific to one or more further chromosomes.
86. Sets of probes according to clause 85, wherein the probes within a set share a custom sequence which is common to that set and differs from the custom sequences of probes in other sets.
87. A kit comprising a set or sets of probes according to any of clauses 82 to 86 in solution in one or more containers.
88. Use of a probe according to any clauses 52 to 81, a set of probes according to any of clauses 82 to 86, or a kit according to clause 87, for testing a sample for the presence of a target nucleic acid fragment.
89. Use of a probe for testing a sample for the presence of a target single stranded nucleic acid fragment,
wherein the probe comprises a targeting oligonucleotide containing a sequence which is the exact complement of the target fragment, and head and tail oligonucleotide sequences which hybridise adjacent to the target fragment on the targeting oligonucleotide,
wherein hybridisation between the target fragment and the probe templates the target fragment for ligation to the head and tail sequences.
90. Use according to clause 89, wherein the probe is as defined in any of clauses 52 to 81.

An embodiment provides a method of processing a nucleic acid sample, comprising: a) hybridizing a sample comprising a target fragment to a nucleic acid probe comprising: i. a head sequence and a tail sequence, wherein the head and tail sequences are at the ends of a first oligonucleotide molecule; and ii. a splint sequence comprising, in order: an upstream flanking sequence that is complementary to the head sequence; a target complementary sequence that is complementary to the target fragment; and a downstream flanking sequence that is complementary to the tail sequence; thereby producing a hybridization product in which the ends of the target fragment are ligatably adjacent to the ends of the head and tail sequences in the first oligonucleotide molecule; and b) ligating the ends of the target fragment to the ends of the head and tail sequences of the first oligonucleotide molecule, thereby producing a cyclic product that comprises the target fragment and the head and tail sequences.

In any embodiment, the method may further comprise amplifying the cyclic product by rolling circle amplification using a primer that hybridizes to the first oligonucleotide molecule or the splint sequence. In these embodiments, the method may further comprise quantify the number of rolling circle amplification products produced, thereby providing an estimate of the amount of said target fragment in the sample.

In some embodiments, the splint sequence may be in the first oligonucleotide molecule.

In some embodiments, the splint sequence may be in a second oligonucleotide molecule.

In any embodiment, the target-complementary sequence may be 10 to 30 nucleotides in length.

In any embodiment, the target-complementary sequence may contains one or more mismatches to the target fragment.

In any embodiment, the flanking sequences may be 10 and 40 nucleotides in length.

In any embodiment, the sample may be digested with a restriction enzyme.

In any embodiment, the sample may comprise genomic DNA, e.g., human genomic DNA. In these embodiments, the sample may comprise cell-free DNA isolated from blood. For example, in any embodiment, the sample may comprise cell-free DNA isolated from the bloodstream of a pregnant human.

In some embodiments, the splint sequence may be in a second oligonucleotide molecule that comprises an capture moiety, e.g., a biotin moiety. In these embodiments, the method may comprise: c) immobilizing the cyclic product by binding the capture moiety to a solid phase; and d) washing the solid phase to remove unligated nucleic acid and other reaction components, thereby enriching for the cyclic product.

In any embodiment, the target fragment may be from chromosome 21, 13 or 18.

In some embodiments, the method may comprise hybridizing the sample with a set of at least 50 of said probes, wherein said probes target different fragments on the same chromosome, and wherein the method results in a plurality of cyclic products that comprise the target fragments.

In these embodiments, the method may comprise hybridizing the sample with a first set and a second set of said sets of probes, wherein the first and second sets target a first chromosome and a second chromosome, respectively, amplifying the cyclic products by rolling circle amplification (RCA) and comparing the number of RCA products corresponding to the first chromosome to the number of RCA products corresponding to the first chromosome.

In these embodiments, the method may comprise hybridizing the sample with a first set and a second set of said sets of probes, wherein the first and second sets target a first and second regions on a chromosome, respectively, amplifying the cyclic products by rolling circle amplification (RCA) and comparing the number of RCA products corresponding to the first region to the number of RCA products corresponding to the second region.

Also provided herein is a composition comprising a nucleic acid probe, as described above. In some embodiments, the nucleic acid probe may comprise: i. a head sequence and a tail sequence, wherein the head and tail sequences are at opposite ends of a first oligonucleotide molecule; and ii. a splint sequence comprising, in order: an upstream flanking sequence that is complementary to the head sequence; a target complementary sequence that is complementary to a target fragment in the human genome; and a downstream flanking sequence that is complementary to the tail sequence; wherein the probe is designed so that, when the first oligonucleotide, the splint sequence, and the target fragment are hybridized to one another, the ends of the target fragment are ligatably adjacent to the ends of the head and tail sequences in the first oligonucleotide molecule.

In any composition embodiment, the composition may comprise a first set of at least 50 of the nucleic acid probes, wherein the target complementary sequences of said probes are complementary to different target fragments of a first human chromosome, e.g., human chromosome is 21, 13 or 18. In these embodiments, the composition may optionally comprise a second set of at least 50 of said nucleic acid probes, wherein the target complementary sequences of said probes of the second set are complementary to different target fragments of a second human chromosome, e.g., chromosomes 13 or 18 (if the first chromosome is chromosome 21).

What is claimed is:

1. A method for producing a circular ligation product, comprising:
   (a) hybridizing:
      (i) denatured human DNA comprising a target fragment;
      (ii) a targeting oligonucleotide comprising:
         an internal target-complementary sequence that is in the range of 10 to 100 nucleotides in length and complementary to the target fragment,
         an upstream flanking sequence of at least 10 nucleotides that is not complementary to human genomic DNA, and
         a downstream flanking sequence of at least 10 nucleotides that is not complementary to human genomic DNA, and
      (iii) a second oligonucleotide comprising a head sequence and a tail sequence, wherein the head sequence and the tail sequence are complementary to the upstream flanking sequence and the downstream flanking sequence, respectively;
      to produce a complex comprising a target fragment, a targeting oligonucleotide and a second oligonucleotide, and
   (b) ligating 5' and 3' ends the target fragment to the 3' and 5' ends of the second oligonucleotide, respectively, to produce a circular ligation product.

2. The method of claim 1, further comprising:
   (c) amplifying the circular ligation product by rolling circle amplification, to produce a rolling circle amplification product.

3. The method of claim 2, further comprising:
   (d) detecting the rolling circle amplification product.

4. The method of claim 3, wherein the rolling circle amplification RCA product is detected by hybridization to a labelled oligonucleotide.

5. The method of claim 1, wherein the denatured human DNA is cell-free DNA that has been digested by a restriction endonuclease and then denatured.

6. The method of claim 5, wherein the cell-free DNA is from the bloodstream of a pregnant woman.

7. The method of claim 1, wherein the internal target-complementary sequence of the targeting oligonucleotide is a sequence from human chromosome 21.

8. The method of claim 1, wherein the internal target-complementary sequence of the targeting oligonucleotide is complementary to a sequence that contains a mutation.

9. The method of claim 1, wherein the head sequence and the tail sequence are joined to a custom sequence, wherein the custom sequence is not complementary to other regions of the probe or to the target fragment.

10. The method of claim 1, wherein the target-complementary sequence has a length in the range of 10 to 40 nucleotides.

11. The method of claim 1, wherein the flanking sequences each independently have a length in the range of 10 to 40 nucleotides.

12. The method of claim 1, wherein, in the product of step (i), at least one of:
   the 3' end of second oligonucleotide and the 5' end of the target fragment do not hybridize to adjacent nucleotides of the targeting oligonucleotide; or,
   the 5' end of second oligonucleotide and the 3' end of the target fragment do not hybridize to adjacent nucleotides of the targeting oligonucleotide.

13. The method of claim 2, wherein, in the product of step (i), at least one of:
   the 3' end of the second oligonucleotide and the 5' end of the target fragment hybridize to adjacent nucleotides of the targeting oligonucleotide; or,
   the 5' end of the second oligonucleotide and the 3' end of the target fragment hybridize to adjacent nucleotides of the targeting oligonucleotide.

14. The method of claim 2, wherein, in the product of step (i), at least one of:
   the upstream flanking sequence is not immediately adjacent to the target-complementary sequence in the targeting oligonucleotide; or,
   the downstream flanking sequence is not immediately adjacent to the target-complementary sequence in the targeting oligonucleotide.

15. The method of claim 2, wherein, in the product of step (i), at least one of:
   the upstream flanking sequence is immediately adjacent to the target-complementary sequence in the targeting oligonucleotide; or,
   the downstream flanking sequence is immediately adjacent to the target-complementary sequence in the targeting oligonucleotide.

* * * * *

UNITED STATES PATENT AND TRADEMARK OFFICE
CERTIFICATE OF CORRECTION

PATENT NO. : 10,731,214 B2
APPLICATION NO. : 16/250892
DATED : August 4, 2020
INVENTOR(S) : Carl Oscar Fredrik Dahl et al.

Page 1 of 1

It is certified that error appears in the above-identified patent and that said Letters Patent is hereby corrected as shown below:

In the Claims

Column 45, Line 35, cancel the text beginning with "4. The method of" to and ending "labelled oligonucleotide." in Column 45, Line 37, and insert the following claim:

--4. The method of claim 3, wherein the rolling circle amplification product is detected by hybridization to a labelled oligonucleotide.--

Signed and Sealed this
Seventeenth Day of November, 2020

Andrei Iancu
*Director of the United States Patent and Trademark Office*

SEQUENCE LISTING

```
<160> NUMBER OF SEQ ID NOS: 3

<210> SEQ ID NO 1
<211> LENGTH: 93
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (31)..(60)
<223> OTHER INFORMATION: n is a, c, g or t and positions 31 to 60
      represent a target complementary sequence on human chromosome 21.

<400> SEQUENCE: 1
atgtgaccct tccgtctgtt gagttaggcc nnnnnnnnnn nnnnnnnnnn nnnnnnnnnn      60
tcgtgccttg tcattcggga gcactaactg ctg                                  93

<210> SEQ ID NO 2
<211> LENGTH: 152
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: c has 5' phosphate
<220> FEATURE:
<221> NAME/KEY: misc_feature
<222> LOCATION: (64)..(73)
<223> OTHER INFORMATION: n is a, c, g, or t

<400> SEQUENCE: 2
cgcacacgat taaggtccag tcacaggcag agatcggaag agcgtcgtgt agggaaagag      60
tgtnnnnnnn nnngtgtaga tctcggtggt cgccgtatca tttcatgctg ctaacggtcg    120
agtcggacag gtggctccac taaatagacg ca                                  152

<210> SEQ ID NO 3
<211> LENGTH: 152
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: g has a 5' phosphate
<220> FEATURE:
<221> NAME/KEY: misc_feature
<222> LOCATION: (64)..(73)
<223> OTHER INFORMATION: n is a, c, g, or t

<400> SEQUENCE: 3
ggcctaactc aacagacgga agggtcacat agatcggaag agcgtcgtgt agggaaagag      60
tgtnnnnnnn nnngtgtaga tctcggtggt cgccgtatca tttcatgctg ctaacggtcg    120
agcagttagt gctcccgaat gacaaggcac ga                                  152
```